(12) United States Patent
Owens et al.

(10) Patent No.: US 6,291,199 B1
(45) Date of Patent: Sep. 18, 2001

(54) HUMAN PHOSPHODIESTERASE TYPE IVC, AND ITS PRODUCTION AND USE

(75) Inventors: Raymond John Owens, Henley-on-Thames; Martin John Perry, Worcester Park; Simon Mark Lumb, Maidenhead, all of (GB)

(73) Assignee: Celltech Therapeutics Limited (GB)

( * ) Notice: Subject to any disclaimer, the term of this patent is extended or adjusted under 35 U.S.C. 154(b) by 0 days.

(21) Appl. No.: 09/079,630

(22) Filed: May 15, 1998

Related U.S. Application Data

(62) Division of application No. 08/577,492, filed on Dec. 22, 1995, now Pat. No. 5,851,784.

(30) Foreign Application Priority Data

Dec. 23, 1994 (GB) .................................................. 9426227
Jun. 26, 1995 (GB) .................................................. 9512996

(51) Int. Cl.[7] .............................. C12Q 1/44; C12P 21/06; C12N 9/16; C07H 21/02; C07H 21/04

(52) U.S. Cl. .......................... 435/19; 435/69.1; 435/196; 536/23.1; 536/23.2; 536/23.5; 536/24.3

(58) Field of Search .................................. 536/23.1, 23.2, 536/24.3, 23.5; 435/69.1, 196, 19

(56) References Cited

U.S. PATENT DOCUMENTS

| | | | |
|---|---|---|---|
| 5,672,509 | * 9/1997 | Fisher | 435/325 |
| 5,686,286 | * 11/1997 | Fisher | 435/199 |

FOREIGN PATENT DOCUMENTS

| | | |
|---|---|---|
| WO 91/09967 | 7/1991 | (WO). |
| WO 91/16457 | 10/1991 | (WO). |

OTHER PUBLICATIONS

Engels et al. (Z46632, GenBank) published in FEBS Letters, 1995, vol. 358(3), pp 305–310 "Molecular cloning and functional expression in yeast of a human cAMP–specific phosphodieterase subtype (PDE IV–C)".*
McLaughlin et al. (1993) J. Biol. Chem. 268/9:6470–76.*
Obernolte et al. (1993) Gene 129:239–47.*
Livi et al. (1990) Molec. Cell. Biol. 10:2678–86.*
Beavo, J.A. et al., "Primary Sequence of Cyclic Nucleotide Phosphodieterase Isozymes and the Design of Selective Inhibitors", *Trends Pharmacol. Sci.*, 1990, 11, 150–155.
Belyauskey et al., "PCR–based cDNA library construction: general cDNA libraries at the level of a few cells", *Nucl. Acids Res.*, 1989, 17(8), 2919–2932.
Bolger, G. et al., "A Family of Human Phosphodieterases Homologous to the dunce Learning and Memory Gene Product of *Drosophila melanogaster* Are Potential Targets for Antidepressant Drugs", *Mol. Cell. Biol.*, 1993, 13(10), 6558–6571.

Cockett, M. et al., "The use of engineered E1A genes to transactivate the hCMV–MIE promoter in permanent CHO cell lines", *Nucl. Acids Res.*, 1991, 19(2), 319–325.
Conti, M. et al., "Characterization of a Hormone–Inducible, High Affinity Adenosine 3'–5'–Cyclic Monophosphate Phosphodieterase from the Rat Sertoli Cell", *Biochemistry*, 1995, 34, 7979–7987.
Conti, M. et al., "Hormonal Regulation of Cyclic Nucleotide Phosphodiesterases", *Endocrine Rev.*, 1991, 12(3), 218–234.
Davis, R. et al., "Cloning and characterization of mammalian homologs of the *Drosophila* dunce+ gene", *Proc. Natl. Acad. Sci. USA*, 1989, 86, 3604–3608.
Dent, G. et al., "Inhibition of eosinophil cyclic nucleotide PDE activity and opsonised zymosan–stimulated respiratory burst by 'type IV'–selective PDE inhibitors", *Br. J. Pharmacol.*, 1991, 103, 1339–1346.
Engles et al., "Molecular cloning and functional expression in yeast of a human cAMP–specific phosphodieterase subtype (PDE IV–C)", *FEBS Lettl.*, 1995, 358, 305–310.
Frohman et al., "Rapid production of full–length cDNAs from rare transcripts: Amplification using a single gene–specific oligonucleotide primer", *Proc. Natl. Acad. Sci. USA*, 1988, 85, 8998–9002.
Gillespie, P.G. et al., "Inhibition and Stimulation of Photoreceptor Phosphodiesterases by Dipyridamole and M&B 22,948", *Mol. Pharmacol.*, 1989, 36, 773–781.
Harrison, S.A. et al., "Isolation and Characterization of Bovine Cardiac Muscle cGMP–Inhibited Phosphodiesterases: A Receptor for New Cardiotonic Drugs", *Mol. Pharmacol.*, 1986, 29, 506–514.
Ito, H. et al., "Transformation of Intact Yeast Cells Treated with Alkali Cations", *J. Bacteriology*, 1983, 53(1), 163–168.
Jin, C. et al., "Characterization of the Structure of a Low $K_m$, Rolipram–sensitive cAMP Phosphodieterase", *J. Biol. Chem.*, 1992, 267(26), 18929–18939.
Kaulen, P. et al., "Autoradiographic Mapping of a selective cyclic adenosine monophosphate phosphodiesterase in rat brain with the antidepressant [$^3$H]rolipram", *Brain Res.*, 1989, 503, 229–245.
Kobilka, B. et al., "Delineation of the Intronless Nature of the Genes for the Human and Hamster β2–Adrenergic Receptor and Their Putative Promotor Regions", *J. Biol. Chem.*, 1987, 262(15), 7321–7327.

(List continued on next page.)

Primary Examiner—Karen Cochrane Carlson
Assistant Examiner—Rita Mitra
(74) *Attorney, Agent, or Firm*—Woodcock Washburn Kurtz Mackiewicz & Norris LLP

(57) ABSTRACT

Recombinant human phosphodiesterase type IVC is described, and DNA coding for it. Particular conformers of the enzyme are identified, including a R- and S-rolipram stereoselective conformer which is obtainable by expression of human phosphodiesterase type IVC DNA in mammalian or insect cells. The recombinant enzyme may be used in a screen to select a compound capable of modulating the action of the enzyme, or as an immunogen to generate an antibody.

1 Claim, 15 Drawing Sheets

OTHER PUBLICATIONS

Kramer et al., "The gapped duplex DNA approach to oligonucleotide–directed mutation construction", *Nucl. Acids. Res.*, 1984, 12(24), 9441–9456.

Laemmli, U.K., "Cleavage of Structural Proteins during the Assembly of the Head of Bacteriophage T4", *Nature*, 1970, 227, 680–685.

Livi et al., "Cloning and Expression of cDNA for a Human Low-$K_m$3 Rolipram–sensitive Cyclic AMP Phosphodiesterase", *Mol. Cell. Biol.*, 1990, 10, 2678–2686.

Londesborough, J. et al., "The Zinc–containing High $K_m$ Cyclic Nucleotide Phosphodieterase of Bakers' Yeast", *J. Biol. Chem.*, 1983, 258(5), 2966–2972.

Mclaughlin, M. et al., "A Low–$K_m$, Rolipram–sensitive, cAMP–specific Phosphodiesterase from Human Brain", *J. Biol. Chem.*, 1993, 268(9), 6470–6476.

Maniatis et al., *Molecular Cloning*, 1989, Cold Spring Harbor Laboratory, New York.

Obernolte, R. et al., "The cDNA of human lymphocyte cyclic–AMP phosphodiesterase (PDE IV) reveals a multigene family", *Gene*, 1993, 129, 239–247.

Peachell, P.T. et al., "Preliminary Identification and Role of Phosphodiesterase Isozymes in Human Basophils", *J. Immunol.*, 1992, 148(8), 2503–2510.

Pillai, R. et al., "Use of a yeast expression system for the isolation and analysis of drug–resistant mutants of a mammalian phosphodiesterase", *Proc. Natl. Acad. Sci. USA*, 1993, 90, 11970–11974.

Sanger F. et al., "DNA sequencing with chain–terminating inhibitors", *Proc. Natl. Acad. Sci. USA*, 1977, 74(12), 5463–5467.

Schmiechen, R. et al., "Close correlation between behavioural response and binding in vivo for inhibitors of the rolipram–sensitive phosphodiesterase", *Psychopharmacology*, 1990, 102, 17–20.

Schneider, H.H. et al., "Stereospecific Binding of the Antidepressant Rolipram to Brain Protein Structures", *Eur. J. Pharmacol.*, 1986, 127, 105–115.

Smith, B.J. et al., "A Phosphodiesterase Assay Using Alumina Microcolumns", *Analyt. Biochem.*, 1993, 214, 355–357.

Sommer, N. et al., "The antidepressant rolipram suppresses cytokine production and prevents autoimmune encephalomyelitis", *Nature Medicine*, 1995, 1(3), 244–248.

Souranta, K. et al., "Purification of Intact and Nicked Forms of a Zinc–containing, $Mg^{2+}$–dependent, Low $K_m$ Cyclic AMP Phosphodiesterase from Bakers' Yeast", *J. Biol. Chem.*, 1984, 259(11), 6964–6971.

Stephens, P. et al., "The construction of a highly efficient and versatile set of mammalian expression vectors", *Nucl. Acids. Res.*, 1989, 17(17), 7110.

Swinnen, J.V. et al., "Molecular cloning of rat homologues of the *Drosophila melanogaster* dunce cAMP phosphodiesterase: Evidence for a family of genes", *Proc. Natl. Acad. Sci. USA*, 1989, 86, 5325–5329.

Swinnen, J.V. et al., "Properties and Hormonal Regulation of Two Structurally Related cAMP Phosphodiesterases from the Rat Sertoli Cell", *J. Biol. Chem.*, 1991, 266(27), 18370–18377.

Torphy, T. et al., "Coexpression of Human cAMP–specific Phosphodiesterase Activity and High Affinity Rolipram Binding in Yeast", *J. Biol. Chem.*, 1992, 267(3), 1798–1804.

Uloa et al., "Cyclic nucleotide phosphodiesterase activity in neurospora crassa: purification by immunoaffinity chromatography and characterization", *FEBS Lett*, 1988, 241, 219–222.

Whittle, N. et al., "Expression in COS cells of a mouse—human chimaeric B72.3 antibody", *Protein Engieering*, 1987, 1(6), 499–505.

Wilson, M. et al., "Purification, characterization and analysis of rolipram inhibition of a human type–IVA cyclic AMP–specific phosphodiesterase expressed in yeast", *Biochem. J.*, 1994, 304, 407–415.

* cited by examiner

FIGURE 1A    SEQUENCE OF HUMAN PDE IVC cDNA.

```
              10             20             30             40
               *              *              *              *
      TTC GAC GTG ATC AGA CCC AAC TCA GAC CCG GTC ATA CTT GGA CCG AAT
      AAG CTG CAC TAG TCT GGG TTG AGT CTG GGC CAG TAT GAA CCT GGC TTA 50             60             70             80             90
           *              *              *              *              *
      GCT GCC AAA TCC CCC ACC TCT ACC CAG ATC TGA GCC TAC GCG GGG TGC
      CGA CGG TTT AGG GGG TGG AGA TGG GTC TAG ACT CGG ATG CGC CCC ACG 100            110            120            130            140
              *              *              *              *              *
      CGA CCC AGC TCG TGG ACG GGG ATA CGG TGA CCT TTG ACC CAA AAG TCT
      GCT GGG TCG AGC ACC TGC CCC TAT GCC ACT GGA AAC TGG GTT TTC AGA 150            160            170            180            190
               *              *              *              *              *
      TGG CCG GGA CCA GCC GGA CAC TGG CCC TCG GCC GGG AGC TCC GAG TCT
      ACC GGC CCT GGT CGG CCT GTG ACC GGG AGC CGG CCC TCG AGG CTC AGA 200            210            220            230            240
               *              *              *              *              *
      CAG GCG GTC CCG GTT GTC TTC CTG TCG GTG CCG CTT CCG CCT GCC CTT
      GTC CGC CAG GGC CAA CAG AAG GAC AGC CAC GGC GAA GGC GGA CGG GAA 250            260            270            280
                *              *              *              *
      CTT GAA AAC CCA CCC CCA GCT TTG ACC TGG AAA ATG GGC TCT CGT GTG
      GAA CTT TTG GGT GGG GGT CGA AAC TGG ACC TTT TAC CCG AGA GCA CAC 290            300            310            320            330
       *              *              *              *              *
      GGA GGA GGG CCC TGG ACC CTC AGT CCA GCC CTG GCC TGG GCC GGA TT ATG
      CCT CCT CCC GGG ACC TGG GAG TCA GGT CGG GAC CGG ACC CGG CCT AA TAC
                                                                        M>
                                                                    ___>

340            350            360            370            380
       *              *              *              *              *
      CAG GCT CCA GTC CCG CAC AGC CAG CGG CGC GAG TCC TTC CTG TAC CGC
      GTC CGA GGT CAG GGC GTG TCG GTC GCC GCG CTC AGG AAG GAC ATG GCG
       Q   A   P   V   P   H   S   Q   R   R   E   S   F   L   Y   R>
      ___a___a___a___a___a___a___a___a___a___a___a___a___a___a___a___>

390            400            410            420            430
       *              *              *              *              *
      TCA GAT AGC GAC TAT GAA CTC TCG CCC AAG GCC ATG TCT CGG AAC TCC
      AGT CTA TCG CTG ATA CTT GAG AGC GGG TTC CGG TAC AGA GCC TTG AGG
       S   D   S   D   Y   E   L   S   P   K   A   M   S   R   N   S>
      ___a___a___a___a___a___a___a___a___a___a___a___a___a___a___a___>
```

FIGURE 1B

```
          440            450            460            470            480
           *              *              *              *              *
   TCT GTG GCC AGC GAC CTA CAT GGA GAG GAC ATG ATT GTG ACG CCC TTT
   AGA CAC CGG TCG CTG GAT GTA CCT CTC CTG TAC TAA CAC TGC GGG AAA
    S   V   A   S   D   L   H   G   E   D   M   I   V   T   P   F>
   ___a___a___a___a___a___a___a___a___a___a___a___a___a___a___a___>

490            500            510            520            530
           *              *              *              *              *
   GCC CAG GTC CTG GCC AGT CTG CGG ACC GTT CGG AGC AAC GTG GCG GCC
   CGG GTC CAG GAC CGG TCA GAC GCC TGG CAA GCC TCG TTG CAC CGC CGG
    A   Q   V   L   A   S   L   R   T   V   R   S   N   V   A   A>
   ___a___a___a___a___a___a___a___a___a___a___a___a___a___a___a___>

540            550            560            570
           *              *              *              *
   CTT GCC CGC CAG CAA TGC CTA GGA GCA GCC AAG CAG GGA CCC GTC GGA
   GAA CGG GCG GTC GTT ACG GAT CCT CGT CGG TTC GTC CCT GGG CAG CCT
    L   A   R   Q   Q   C   L   G   A   A   K   Q   G   P   V   G>
   ___a___a___a___a___a___a___a___a___a___a___a___a___a___a___a___>

580            590            600            610            620
   *              *              *              *              *
   AAC CCT TCA TCC AGC AAT CAG CTC CCT CCT GCA GAG GAC ACG GGG CAG
   TTG GGA AGT AGG TCG TTA GTC GAG GGA GGA CGT CTC CTG TGC CCC GTC
    N   P   S   S   S   N   Q   L   P   P   A   E   D   T   G   Q>
   ___a___a___a___a___a___a___a___a___a___a___a___a___a___a___a___>

630            640            650            660            670
           *              *              *              *              *
   AAG CTG GCA TTG GAG ACG CTA GAC GAG CTG GAC TGG TGC CTG GAT CAG
   TTC GAC CGT AAC CTC TGC GAT CTG CTC GAC CTG ACC ACG GAC CTA GTC
    K   L   A   L   E   T   L   D   E   L   D   W   C   L   D   Q>
   ___a___a___a___a___a___a___a___a___a___a___a___a___a___a___a___>

680            690            700            710            720
           *              *              *              *              *
   TTG GAG ACG CTG CAG ACC CGG CAC TCG GTG GGG GAG ATG GCC TCC AAC
   AAC CTC TGC GAC GTC TGG GCC GTG AGC CAC CCC CTC TAC CGG AGG TTG
    L   E   T   L   Q   T   R   H   S   V   G   E   M   A   S   N>
   ___a___a___a___a___a___a___a___a___a___a___a___a___a___a___a___>

730            740            750            760            770
           *              *              *              *              *
   AAG TTC AAG CGG ATC CTG AAC CGG GAG TTG ACC CAC CTG TCC GAA ACC
   TTC AAG TTC GCC TAG GAC TTG GCC CTC AAC TGG GTG GAC AGG CTT TGG
    K   F   K   R   I   L   N   R   E   L   T   H   L   S   E   T>
   ___a___a___a___a___a___a___a___a___a___a___a___a___a___a___a___>

780            790            800            810
           *              *              *              *
   AGC CGC TCC GGG AAC CAG GTG TCC GAG TAC ATC TCC CGG ACC TTC CTG
   TCG GCG AGG CCC TTG GTC CAC AGG CTC ATG TAG AGG GCC TGG AAG GAC
    S   R   S   G   N   Q   V   S   E   Y   I   S   R   T   F   L>
   ___a___a___a___a___a___a___a___a___a___a___a___a___a___a___a___>
```

FIGURE 1C

```
        820         830         840         850         860
         *           *           *           *           *
GAC CAG CAG ACC GAG GTG GAG CTG CCC AAG GTG ACC GCT GAG GAG GCC
CTG GTC GTC TGG CTC CAC CTC GAC GGG TTC CAC TGG CGA CTC CTC CGG
 D   Q   Q   T   E   V   E   L   P   K   V   T   A   E   E   A>
___a___a___a___a___a___a___a___a___a___a___a___a___a___a___a___>

870         880         890         900         910
         *           *           *           *           *
CCA CAG CCC ATG TCC CGG ATC AGT GGC CTA CAT GGG CTC TGC CAC AGT
GGT GTC GGG TAC AGG GCC TAG TCA CCG GAT GTA CCC GAG ACG GTG TCA
 P   Q   P   M   S   R   I   S   G   L   H   G   L   C   H   S>
___a___a___a___a___a___a___a___a___a___a___a___a___a___a___a___>

920         930         940         950         960
         *           *           *           *           *
GCC AGC CTC TCC TCA GCC ACT GTC CCA CGC TTT GGG GTC CAG ACT GAC
CGG TCG GAG AGG AGT CGG TGA CAG GGT GCG AAA CCC CAG GTC TGA CTG
 A   S   L   S   S   A   T   V   P   R   F   G   V   Q   T   D>
___a___a___a___a___a___a___a___a___a___a___a___a___a___a___a___>

970         980         990        1000        1010
         *           *           *           *           *
CAG GAG GAG CAA CTG GCC AAG GAG CTA GAA GAC ACC AAC AAG TGG GGA
GTC CTC CTC GTT GAC CGG TTC CTC GAT CTT CTG TGG TTG TTC ACC CCT
 Q   E   E   Q   L   A   K   E   L   E   D   T   N   K   W   G>
___a___a___a___a___a___a___a___a___a___a___a___a___a___a___a___>

1020        1030        1040        1050
         *           *           *           *
CTT GAT GTG TTC AAG GTG GCG GAG CTA AGT GGG AAC CAG CCC CTC ACA
GAA CTA CAC AAG TTC CAC CGC CTC GAT TCA CCC TTG GTC GGG GAG TGT
 L   D   V   F   K   V   A   E   L   S   G   N   Q   P   L   T>
___a___a___a___a___a___a___a___a___a___a___a___a___a___a___a___>

1060        1070        1080        1090        1100
  *           *           *           *           *
GCT ATC ATA TTC AGC ATT TTT CAG GAG CGG GAC CTG CTG AAG ACA TTC
CGA TAG TAT AAG TCG TAA AAA GTC CTC GCC CTG GAC GAC TTC TGT AAG
 A   I   I   F   S   I   F   Q   E   R   D   L   L   K   T   F>
___a___a___a___a___a___a___a___a___a___a___a___a___a___a___a___>

1110        1120        1130        1140        1150
         *           *           *           *           *
CAG ATC CCA GCA GAC ACA CTG GCC ACC TAC CTG CTG ATG CTG GAG GGT
GTC TAG GGT CGT CTG TGT GAC CGG TGG ATG GAC GAC TAC GAC CTC CCA
 Q   I   P   A   D   T   L   A   T   Y   L   L   M   L   E   G>
___a___a___a___a___a___a___a___a___a___a___a___a___a___a___a___>

1160        1170        1180        1190        1200
         *           *           *           *           *
CAC TAC CAC GCC AAT GTG GCC TAC CAC AAC AGC CTA CAT GCC GCC GAC
GTG ATG GTG CGG TTA CAC CGG ATG GTG TTG TCG GAT GTA CGG CGG CTG
 H   Y   H   A   N   V   A   Y   H   N   S   L   H   A   A   D>
___a___a___a___a___a___a___a___a___a___a___a___a___a___a___a___>
```

FIGURE 1D

```
            1210           1220           1230           1240           1250
              *              *              *              *              *
    GTG GCC CAG TCC ACG CAT GTG CTG CTG GCT ACG CCC GCC CTC GAG GCT
    CAC CGG GTC AGG TGC GTA CAC GAC GAC CGA TGC GGG CGG GAG CTC CGA
     V   A   Q   S   T   H   V   L   L   A   T   P   A   L   E   A>
    ___a___a___a___a___a___a___a___a___a___a___a___a___a___a___a___>

1260           1270           1280           1290
              *              *              *              *
    GTG TTC ACA GAC TTG GAA ATC CTG GCT GCC CTC TTT GCA AGC GCC ATC
    CAC AAG TGT CTG AAC CTT TAG GAC CGA CGG GAG AAA CGT TCG CGG TAG
     V   F   T   D   L   E   I   L   A   A   L   F   A   S   A   I>
    ___a___a___a___a___a___a___a___a___a___a___a___a___a___a___a___>

1300           1310           1320           1330           1340
   *              *              *              *              *
 CAC GAC GTG GAC CAT CCT GGG GTC TCC AAC CAG TTT CTG ATT AAC ACC
 GTG CTG CAC CTG GTA GGA CCC CAG AGG TTG GTC AAA GAC TAA TTG TGG
  H   D   V   D   H   P   G   V   S   N   Q   F   L   I   N   T>
 ___a___a___a___a___a___a___a___a___a___a___a___a___a___a___a___>

1350           1360           1370           1380           1390
            *              *              *              *              *
  AAC TCA GAG CTG GCG CTT ATG TAC AAC GAC GCC TCG GTC CTG GAG AAC
  TTG AGT CTC GAC CGC GAA TAC ATG TTG CTG CGG AGC CAC GAC CTC TTG
   N   S   E   L   A   L   M   Y   N   D   A   S   V   L   E   N>
  ___a___a___a___a___a___a___a___a___a___a___a___a___a___a___a___>

1400           1410           1420           1430           1440
            *              *              *              *              *
  CAT CAC CTG GCT GTG GGC TTC AAG CTG CTG CAG GCA GAG AAC TGC GAT
  GTA GTG GAC CGA CAC CCG AAG TTC GAC GAC GTC CGT CTC TTG ACG CTA
   H   H   L   A   V   G   F   K   L   L   Q   A   E   N   C   D>
  ___a___a___a___a___a___a___a___a___a___a___a___a___a___a___a___>

1450           1460           1470           1480           1490
            *              *              *              *              *
  ATC TTC CAG AAC CTC AGC GCC AAG CAG CGA CTG AGT CTG CGC AGG ATG
  TAG AAG GTC TTG GAG TCG CGG TTC GTC GCT GAC TCA GAC GCG TCC TAC
   I   F   Q   N   L   S   A   K   Q   R   L   S   L   R   R   M>
  ___a___a___a___a___a___a___a___a___a___a___a___a___a___a___a___>

1500           1510           1520           1530
               *              *              *              *
     GTC ATT GAC ATG GTG CTG GCC ACA GAC ATG TCC AAA CAC ATG AAC CTC
     CAG TAA CTG TAC CAC GAC CGG TGT CTG TAC AGG TTT GTG TAC TTG GAG
      V   I   D   M   V   L   A   T   D   M   S   K   H   M   N   L>
     ___a___a___a___a___a___a___a___a___a___a___a___a___a___a___a___>

1540           1550           1560           1570           1580
   *              *              *              *              *
 CTG GCC GAC CTC AAG ACC ATG GTG GAG ACC AAG AAG GTG ACA AGC CTC
 GAC CGG CTG GAG TTC TGG TAC CAC CTC TGG TTC TTC CAC TGT TCG GAG
  L   A   D   L   K   T   M   V   E   T   K   K   V   T   S   L>
 ___a___a___a___a___a___a___a___a___a___a___a___a___a___a___a___>
```

FIGURE 1E

```
         1590        1600        1610        1620        1630
           *           *           *           *           *
     GGT GTC CTC CTC CTG GAC AAC TAT TCC GAC CGA ATC CAG GTC TTG CAG
     CCA CAG GAG GAG GAC CTG TTG ATA AGG CTG GCT TAG GTC CAG AAC GTC
      G   V   L   L   L   D   N   Y   S   D   R   I   Q   V   L   Q>
     ___a___a___a___a___a___a___a___a___a___a___a___a___a___a___a___>

1640        1650        1660        1670        1680
           *           *           *           *           *
     AAC CTG GTG CAC TGT GCT GAT CTG AGC AAC CCC ACC AAG CCG CTG CCC
     TTG GAC CAC GTG ACA CGA CTA GAC TCG TTG GGG TGG TTC GGC GAC GGG
      N   L   V   H   C   A   D   L   S   N   P   T   K   P   L   P>
     ___a___a___a___a___a___a___a___a___a___a___a___a___a___a___a___>

1690        1700        1710        1720        1730
           *           *           *           *           *
     CTG TAC CGC CAG TGG ACG GAC CGC ATC ATG GCC GAG TTC TTC CAG CAG
     GAC ATG GCG GTC ACC TGC CTG GCG TAG TAC CGG CTC AAG AAG GTC GTC
      L   Y   R   Q   W   T   D   R   I   M   A   E   F   F   Q   Q>
     ___a___a___a___a___a___a___a___a___a___a___a___a___a___a___a___>

1740        1750        1760        1770
                *           *           *           *
         GGA GAC CGC GAG CGT GAG TCG GGC CTG GAC ATC AGT CCC ATG TGT GAC
         CCT CTG GCG CTC GCA CTC AGC CCG GAC CTG TAG TCA GGG TAC ACA CTG
          G   D   R   E   R   E   S   G   L   D   I   S   P   M   C   D>
         ___a___a___a___a___a___a___a___a___a___a___a___a___a___a___a___>

1780        1790        1800        1810        1820
       *           *           *           *           *
     AAG CAT ACG GCC TCA GTG GAG AAG TCC CAG GTG GGT TTC ATT GAC TAC
     TTC GTA TGC CGG AGT CAC CTC TTC AGG GTC CAC CCA AAG TAA CTG ATG
      K   H   T   A   S   V   E   K   S   Q   V   G   F   I   D   Y>
     ___a___a___a___a___a___a___a___a___a___a___a___a___a___a___a___>

1830        1840        1850        1860        1870
           *           *           *           *           *
     ATT GCT CAC CCA CTG TGG GAG ACT TGG GCT GAC CTG GTC CAC CCA GAT
     TAA CGA GTG GGT GAC ACC CTC TGA ACC CGA CTG GAC CAG GTG GGT CTA
      I   A   H   P   L   W   E   T   W   A   D   L   V   H   P   D>
     ___a___a___a___a___a___a___a___a___a___a___a___a___a___a___a___>

1880        1890        1900        1910        1920
           *           *           *           *           *
     GCA CAG GAC CTG CTG GAC ACG CTG GAG GAC AAT CGA GAG TGG TAC CAG
     CGT GTC CTG GAC GAC CTG TGC GAC CTC CTG TTA GCT CTC ACC ATG GTC
      A   Q   D   L   L   D   T   L   E   D   N   R   E   W   Y   Q>
     ___a___a___a___a___a___a___a___a___a___a___a___a___a___a___a___>

1930        1940        1950        1960        1970
           *           *           *           *           *
     AGC AAG ATC CCC CGA AGT CCC TCA GAC CTC ACC AAC CCC GAG CGG GAC
     TCG TTC TAG GGG GCT TCA GGG AGT CTG GAG TGG TTG GGG CTC GCC CTG
      S   K   I   P   R   S   P   S   D   L   T   N   P   E   R   D>
     ___a___a___a___a___a___a___a___a___a___a___a___a___a___a___a___>
```

FIGURE 1F

```
          1980            1990            2000            2010
           *               *               *               *
GGG CCT GAC AGA TTC CAG TTT GAA CTG ACT CTG GAG GAG GCA GAG GAA
CCC GGA CTG TCT AAG GTC AAA CTT GAC TGA GAC CTC CTC CGT CTC CTT
 G   P   D   R   F   Q   F   E   L   T   L   E   E   A   E   E>
 ___a___a___a___a___a___a___a___a___a___a___a___a___a___a___a___>

2020            2030            2040            2050            2060
 *               *               *               *               *
GAG GAT GAG GAG GAA GAA GAG GAG GGG GAA GAG ACA GCT TTA GCC AAA
CTC CTA CTC CTC CTT CTT CTC CTC CCC CTT CTC TGT CGA AAT CGG TTT
 E   D   E   E   E   E   E   E   G   E   E   T   A   L   A   K>
 ___a___a___a___a___a___a___a___a___a___a___a___a___a___a___a___>

2070            2080            2090            2100            2110
      *               *               *               *               *
   GAG GCC TTG GAG TTG CCT GAC ACT GAA CTC CTG TCC CCT GAA GCC GGC
   CTC CGG AAC CTC AAC GGA CTG TGA CTT GAG GAC AGG GGA CTT CGG CCG
    E   A   L   E   L   P   D   T   E   L   L   S   P   E   A   G>
    ___a___a___a___a___a___a___a___a___a___a___a___a___a___a___a___>

2120            2130            2140            2150            2160
         *               *               *               *               *
      CCA GCC CCT GGG GAC TTA CCC CTC GAC AAC CAG AGG ACT TAG GAA TTC
      GGT CGG GGA CCC CTG AAT GGG GAG CTG TTG GTC TCC TGA ATC CTT AAG
       P   A   P   G   D   L   P   L   D   N   Q   R   T   *   E   F>
       ___a___a___a___a___a___a___a___a___a___a___a___a___a___a___a___>
```

FIGURE 2A   ALIGNMENTS OF HUMAN PDE IV AMINO ACID SEQUENCES.

```
GENE A   MEPPTVPSERSLSLSLPGPREGQATLKPPPQHLWRQPRTPIRIQQRGY

GENE A   SDSAERAERERQPHRPIERADAMDTSDRPGLRTTRMSWPSSFHGTGTGSGGAGGSSRRFEAENGTSA
GENE B2                            MKEHGGTFSSTGISGGSGDSAMDSLQPLQPNYM..........
GENE C
GENE D                                              MMHVNNFPFRRHSWICFDVDNGTSA

GENE A   GRSPLDPMTSPSPGLVLHAGAATSQRRESFLYRSDSDYDMSPKTMSRNSSVTSEAHAEDLIVTPFAQV
GENE B2  ..............................................................
GENE C          MQAPVPHSQRRESFLYRSDSDYELSPKAMSRNSSVASDLHGEDMIVTPFAQV
GENE D   GRSPLDPMTSPGSGLILQANFVHSQRRESFLYRSDSDYDLSPKSMSRNSSIASDIHGDDLIVTPFAQV

GENE A   LASLRSVVRSNFSLLTNVPVP.SNKRSPLGGPT.PVCKATLSEETCQQLARETLEELDWCLEQLETMQT
GENE B2  .........................................PVCLFA..EESYQKLAMETLEELDWCLDQLETIQT
GENE C   LASLRTVRSNVAALARQQCLGAAKQGPVGNPSSSNQ.LPPAEDTGQKLALETLDELDWCLDQLETLQT
GENE D   LASLRTVRNNFAALTNLQDRAPSKRSPMCNQPSIN.KATITEEAYQKLASETLEELDWCLDQLETLQT

GENE A   YRSVSEMASHKFKRMLNRELTHLSEMSRSGNQVSEYISTTFLDKQNEVEIPSPTMKEREKQQAPRPRP
GENE B2  YRSVSEMASNKFKRMLNRELTHLSEMSRSGNQVSEVISNTFLDKQNDVEIPSPTQKDREK....KKKQ
GENE C   RHSVGEMASNKFKRILNRELTHLSETSRSGNQVSEYISRTFLDQQTEVELP.......KVTAEEAPQ
GENE D   RHSVSEMASNKFKRMLNRELTHLSEMSRSGNQVSEFISNTFLDKQHEVEIPSPTQKEKEK...KKR.
```

FIGURE 2B

```
GENE A    SPPPPPVPH LQPMSQITGLKKLMHSNSLNNSNIPRFGVKTDQEELLAQELENLNKWGLNIFCVSDYA
GENE B2   Q........ ..LMTQISGVKKLMHSSSLNNTSISRFGVNTENEDHLAKELEDLNKWGLNIFNVAGYS
GENE C    ......... ....PMSRISGLHGLCHSASLSSATVPRFGVQTDQEEQLAKELEDTNKWGLDVFKVAELS
GENE D    ......... ....PMSQISGVKKLMHSSSLTNSSIPRFGVKTEQEDVLAKELEDVNKWGLHVFRIAELS

GENE A    GGRSLTCIMYMIFQERDLLKKFRIPVDTMVTYMLTLEDHYHADVAYHNSLHAADVLQSTHVLLATPAL
GENE B2   HNRPLTCIMYAIFQERDLLKTFRISSDTFITYMMTLEDHYHSDVAYHNSLHAADVAQSTHVLLSTPAL
GENE C    GNQPLTAIIFSIFQERDLLKTFQIPADTLATYLLMLEGHYHANVAYHNSLHAADVAQSTHVLLATPAL
GENE D    GNRPLTVIMHTIFQERDLLKTFKIPVDTLITYLMTLEDHYHADVAYHNNIHAADVVQSTHVLLSTPAL

GENE A    DAVFTDLEILAALFAAAIHDVDHPGVSNQFLINTNSELALMYNDESVLENHHLAVGFKLLQEENCDIF
GENE B2   DAVFTDLEILAAIFAAAIHDVDHPGVSNQFLINTNSELALMYNDESVLENHHLAVGFKLLQEEHCDIF
GENE C    EAVFTDLEILAALFASAIHDVDHPGVSNQFLINTNSELALMYNDASVLENHHLAVGFKLLQAENCDIF
GENE D    EAVFTDLEILAAIFASAIHDVDHPGVSNQFLINTNSELALMYNDSSVLENHHLAVGFKLLQEENCDIF

GENE A    QNLSKRQRQSLRKMVIDMVLATDMSKHMTLLADLKTMVETKKVTSSGVLLLDNYSDRIQVLRNMVHCA
GENE B2   MNLTKKQRQTLRKMVIDMVLATDMSKHMSLLADLKTMVETKKVTSSGVLLLDNYTDRIQVLRNMVHCA
GENE C    QNLSAKQRLSLRRMVIDMVLATDMSKHMNLLADLKTMVETKKVTSLGVLLLDNYSDRIQVLQNLVHCA
GENE D    QNLTKKQRQSLRKMVIDIVLATDMSKHMNLLADLKTMVETKKVTSSGVLLLDNYSDRIQVLQNMVHCA

GENE A    DLSNPTKPLELYRQWTDRIMAEFFQQGDRERERGMEISPMCDKHTASVEKSQVGFIDYIVHPLWETWA
GENE B2   DLSNPTKSLELYRQWTDRIMEEFFQQGDKERERGMEISPMCDKHTASVEKSQVGFIDYIVHPLWETWA
GENE C    DLSNPTKPLPLYRQWTDRIMAEFFQQGDRERESGLDISPMCDKHTASVEKSQVGFIDYIAHPLWETWA
GENE D    DLSNPTKPLQLYRQWTDRIMEEFFRQGDRERERGMEISPMCDKHNASVEKSQVGFIDYIVHPLWETWA
```

FIGURE 2C

```
GENE A    DLVHPDAQEILDTLEDNRDWYYSAIRQSPSPPPEEESRGPGHPPLPDKFQFELTLEEEEISRAQ
GENE B2   DLVQPDAQDILDTLEDNRNWYQSMIPQSPSPPLDEQNRDCQG..LMEKFQFELTLDEEDSEGPEKEG
GENE C    DLVHPDAQDLLDTLEDNREWYQSKIPRSPSDLTNPERDGPDR......FQFELTLEEAEEEDEEEE
GENE D    DLVHPDAQDILDTLEDNREWYQSTIPQSPSPAPDDPEEGRQGQTG..KFQFELTLEEDGESDTEKDS

GENE A    IRCTAQEALTEQGLSGVEEALDATIAWEASPAQESLEVMAQEASLEAELEAVYLTQQAQSTGSEPVA
GENE B2   EGHSYFSSTKTLCVIDPENRDSLGETDIDIATEDKSPVDT*
GENE C    EGEETALAKEALELPDTELLSPEAGPAPGDLPLDNQRT*
GENE D    GSQVEEDTSCSDSKTLCTQDSESTEI PLDEQVEEEAVGEEEESQPEACVIDDRSPDT*

GENE A    PDEFSNREEFVVAVSHSSPSALALQSPLLPAWRTLSVSEHAPGLPGLPSTAAEVEAQREHQAAKRACS

GENE A    ACAGTFGEDTSALPAPGGGGSGGDPT*
```

FIGURE 3    ALIGNMENT OF HUMAN AND RAT PDE IVC AMINO ACID SEQUENCES

```
huC.pep    ETL EEL DWC LDQ LET LQT RHS VGE MAS NKF KRI LNR ELT HLS ETS RSG
ratC.pep   ETL EEL DWC LeQ LET LQT RrS VGE MAS NKF KRm LNR ELT HLS ETS RSG> huC.pep    NQV SEY ISR TFL DQQ TEV ELF Kvt aee apq pms ris gLH GLC HS
ratC.pep   NQV SEY ISq TFL DQQ aEV ELP a.......................lLr ksC Ht> huC.pep    SAT VPR FGV QTD QEE QLA KEL EDT NKW GLD VFK VAE LSG NQP LTA IIF
ratC.pep   tAa iPR FGV QTD QEE QLA KEL EDT NKW GLD VFK VAE LSG NrP LTA vIF> huC.pep    SIF QER DLL KTF QIP ADT LAT YLL MLE GHY HAN VAY HNS LHA ADV AQS
ratC.pep   rvl QER DLL KTF QIP ADT LlR YLL tLE GHY HsN VAY HNS iHA ADV vQS> huC.pep    THV LLA TPA LEA VFT DLE ILA ALF ASA IHD VDH PGV SNQ FLI NTN SEL
ratC.pep   aHV LLg TPA LEA VFT DLE vLA AiF AcA IHD VDH PGV SNQ FLI NTN SEL> huC.pep    ALM YND ASV LEN HHL AVG FKL LQA ENC DIF QNL SAK QRL SLR RMV IDM
ratC.pep   ALM YND sSV LEN HHL AVG FKL LQg ENC DIF QNL StK QkL SLR RMV IDM> huC.pep    VLA TDM SKH MNL LAD LKT MVE TKK VTS LGV LLL DNY SDR IQV LQN LVH
ratC.pep   VLA TDM SKH MsL LAD LKT MVE TKK VTS LGV LLL DNY SDR IQV LQs LVH> huC.pep    CAD LSN PTK PLP LYR QWT DRI MAE FFQ QGD RER ESG LDI SPM CDK HTA
ratC.pep   CAD LSN PaK PLP LYR QWT eRI MAE FFQ QGD RER ESG LDI SPM CDK HTA> huC.pep    SVE KSQ VGF IDY IAH PLW ETW ADL VHP DAQ DLL DTL EDN REW YQS KIP
ratC.pep   SVE KSQ VGF IDY IAH PLW ETW ADL VHP DAQ eLL DTL EDN REW YQS rvP> huC.pep    RSP SDL TNP ERD GPD RFQ FEL TLE EAE EED EEE GEE TAL AKE ALE
ratC.pep   ..........P ERD GPD RFQ FEL TLE EAE EED EEE huC.pep    LPD TEL LSP EAG PAP GDL PLD NQR T
```

Separation of recombinant PDE IVC from yeast PDE activity by monoQ Sepharose ion-exchange chromatography

```
GCT GTC CAG AAA AGG TCC CGC GCA GTC GGC GCT CGG TCC AGC
CGA CAG GTC TTT TCC AGG GCG CGT CAG CCG CGA GCC AGG TCG
 A   V   Q   K   R   S   R   A   V   G   A   R   S   S>
___a___a_._a___a___a___a___a___a___a___a___a___a___a___>

CTC CAC GCA GTC CTG GCG ATG CAG GGC CCC CCC GCG CCC GCC
GAG GTG CGT CAG GAC CGC TAC GTC CCG GGG GGG CGC GGG CGG
 L   H   A   V   L   A   M   Q   G   P   P   A   P   A>
___a___a___a___a___a___a___a___a___a___a___a___a___a___>

100
                       *
CCG GTC CCC GGG CCC GGC TCC CCT CGG GGA TCC CCG CGC GGC
GGC CAG GGG CCC GGG CCG AGG GGA GCC CCT AGG GGC GCG CCG
 P   V   P   G   P   G   S   P   R   G   S   P   R   G>
___a___a___a___a___a___a___a___a___a___a___a___a___a___>

TCC CCC GGG CTC TTC AGG AAG CTT TTG GTG AAT CAG AGC ATC
AGG GGG CCC GAG AAG TCC TTC GAA AAC CAC TTA GTC TCG TAG
 S   P   G   L   F   R   K   L   L   V   N   Q   S   I>
___a___a___a___a___a___a___a___a___a___a___a___a___a___>

200
                                 *
CGC CTG CAG CGG CGC TTC ACG GTG GCC CAT CCG CTG TGC TTT
GCG GAC GTC GCC GCG AAG TGC CAC CGG GTA GGC GAC ACG AAA
 R   L   Q   R   R   F   T   V   A   H   P   L   C   F>
___a___a___a___a___a___a___a___a___a___a___a___a___a___>

GAC CTG GAA AAT GGG CTC TCG TGT GGG AGG AGG GCC CTG GAC
CTG GAC CTT TTA CCC GAG AGC ACA CCC TCC TCC CGG GAC CTG
 D   L   E   N   G   L   S   C   G   R   R   A   L   D>
___a___a___a___a___a___a___a___a___a___a___a___a___a___>

CCT CAG TCC AGC CCT GGC CTG GGC CGG ATT ATG CAG GCT CCA
GGA GTC AGG TCG GGA CCG GAC CCG GCC TAA TAC GTC CGA GGT
 P   Q   S   S   P   G   L   G   R   I   M   Q   A   P>
___a___a___a___a___a___a___a___a___a___a___a___a___a___>

300
       *
GTC CCG CAC AGC CAG CGG CGC GAG TCC TTC CTG TAC CGC TCA
CAG GGC GTG TCG GTC GCC GCG CTC AGG AAG GAC ATG GCG AGT
 V   P   H   S   Q   R   R   E   S   F   L   Y   R   S>
___a___a___a___a___a___a___a___a___a___a___a___a___a___>
```

Figure 7 Sequence of alternative 5' end of
         human PDE IVC mRNA. The sequence
         that differs from the one shown in
         figure 1 is underlined.

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
        (A) LENGTH: 44 bases
        (B) TYPE: nucleic acid
        (C) STRANDEDNESS: single
        (D) TOPOLOGY: linear (xi) SEQUENCE DESCRIPTION: SEQ ID NO:1:

GATCGGATCC GCGGCTGCCA TCCACGATGT GGATCACCCT GGGG                          44

(2) INFORMATION FOR SEQ ID NO:2:

(i) SEQUENCE CHARACTERISTICS:
        (A) LENGTH: 29 bases
        (B) TYPE: nucleic acid
        (C) STRANDEDNESS: single
        (D) TOPOLOGY: linear (xi) SEQUENCE DESCRIPTION: SEQ ID NO:2:

TTTTTGGATC CGGGATCAGG TAGGGTCTC                                           29

(2) INFORMATION FOR SEQ ID NO:3:

(i) SEQUENCE CHARACTERISTICS:
        (A) LENGTH: 31 bases
        (B) TYPE: nucleic acid
        (C) STRANDEDNESS: single
        (D) TOPOLOGY: linear (xi) SEQUENCE DESCRIPTION: SEQ ID NO:3:

TTTTTAAGCT TCAGCTCATG ACCCAGATAA G                                        31

(2) INFORMATION FOR SEQ ID NO:4:

(i) SEQUENCE CHARACTERISTICS:
        (A) LENGTH: 29 bases
        (B) TYPE: nucleic acid
        (C) STRANDEDNESS: single
        (D) TOPOLOGY: linear (xi) SEQUENCE DESCRIPTION: SEQ ID NO:4:

TTTGGATCCG ATAGAATGTT CATCTCCAC                                           29

(2) INFORMATION FOR SEQ ID NO:5:

(i) SEQUENCE CHARACTERISTICS:
        (A) LENGTH: 34 bases
        (B) TYPE: nucleic acid
        (C) STRANDEDNESS: single
        (D) TOPOLOGY: linear (xi) SEQUENCE DESCRIPTION: SEQ ID NO:5:

TTTTTGAATT CGATATCTTC CAGAACCTCA GCGC                                     34

(2) INFORMATION FOR SEQ ID NO:6:

(i) SEQUENCE CHARACTERISTICS:
        (A) LENGTH: 32 bases
        (B) TYPE: nucleic acid
        (C) STRANDEDNESS: single (D) TOPOLOGY: linear (xi) SEQUENCE DESCRIPTION: SEQ ID NO:6:

TTTTTGAATT CCTAAGTCCT CTGGTTGTCG AG                                    32

(2) INFORMATION FOR SEQ ID NO:7:

(i) SEQUENCE CHARACTERISTICS:
            (A) LENGTH: 31 bases
            (B) TYPE: nucleic acid
            (C) STRANDEDNESS: single
            (D) TOPOLOGY: linear (xi) SEQUENCE DESCRIPTION: SEQ ID NO:7:

TTTTTGAATT CAGAGTTGTC TGGTAACCGG C                                     31

(2) INFORMATION FOR SEQ ID NO:8:

(i) SEQUENCE CHARACTERISTICS:
            (A) LENGTH: 29 bases
            (B) TYPE: nucleic acid
            (C) STRANDEDNESS: single
            (D) TOPOLOGY: linear (xi) SEQUENCE DESCRIPTION: SEQ ID NO:8:

TTTTGAATTC GTTACGTGTC AGGAGAACG                                        29

(2) INFORMATION FOR SEQ ID NO:9:

(i) SEQUENCE CHARACTERISTICS:
            (A) LENGTH: 45 bases
            (B) TYPE: nucleic acid
            (C) STRANDEDNESS: single
            (D) TOPOLOGY: linear (xi) SEQUENCE DESCRIPTION: SEQ ID NO:9:

CGCGCGAAGC TTATGGAGAC GCTGGAGGAR YTRGACTGGT GTATG                      45

(2) INFORMATION FOR SEQ ID NO:10:

(i) SEQUENCE CHARACTERISTICS:
            (A) LENGTH: 36 bases
            (B) TYPE: nucleic acid
            (C) STRANDEDNESS: single
            (D) TOPOLOGY: linear (xi) SEQUENCE DESCRIPTION: SEQ ID NO:10:

TTTCTCGAGG GTTTCGGACA GGTGGGTCAA CTCCCG                                36

(2) INFORMATION FOR SEQ ID NO:11:

(i) SEQUENCE CHARACTERISTICS:
            (A) LENGTH: 33 bases
            (B) TYPE: nucleic acid
            (C) STRANDEDNESS: single
            (D) TOPOLOGY: linear (xi) SEQUENCE DESCRIPTION: SEQ ID NO:11:

TTTCTCGAGG CCACTGATCC GGGACATGGG CTG                                   33

(2) INFORMATION FOR SEQ ID NO:12:

(i) SEQUENCE CHARACTERISTICS:
            (A) LENGTH: 33 bases
            (B) TYPE: nucleic acid
            (C) STRANDEDNESS: single
            (D) TOPOLOGY: linear (xi) SEQUENCE DESCRIPTION: SEQ ID NO:12:

TTTCTCGAGC CACTTGTTGG TGTCTTCTAG CTC                33

(2) INFORMATION FOR SEQ ID NO:13:

(i) SEQUENCE CHARACTERISTICS:
        (A) LENGTH: 32 bases
        (B) TYPE: nucleic acid
        (C) STRANDEDNESS: single
        (D) TOPOLOGY: linear (xi) SEQUENCE DESCRIPTION: SEQ ID NO:13:

TTTGGATCCG GCCAGGACCT GGGCAAAGGG CG                 32

(2) INFORMATION FOR SEQ ID NO:14:

(i) SEQUENCE CHARACTERISTICS:
        (A) LENGTH: 35 bases
        (B) TYPE: nucleic acid
        (C) STRANDEDNESS: single
        (D) TOPOLOGY: linear (xi) SEQUENCE DESCRIPTION: SEQ ID NO:14:

TTTGGATCCG GCCTTGGGCG AGAGTTCATA GTCGC              35

(2) INFORMATION FOR SEQ ID NO:15:

(i) SEQUENCE CHARACTERISTICS:
        (A) LENGTH: 34 bases
        (B) TYPE: nucleic acid
        (C) STRANDEDNESS: single
        (D) TOPOLOGY: linear (xi) SEQUENCE DESCRIPTION: SEQ ID NO:15:

TTTTTAAGCT TGACCTCTGT CCCTGTTCCC CTCC               34

(2) INFORMATION FOR SEQ ID NO:16:

(i) SEQUENCE CHARACTERISTICS:
        (A) LENGTH: 34 bases
        (B) TYPE: nucleic acid
        (C) STRANDEDNESS: single
        (D) TOPOLOGY: linear (xi) SEQUENCE DESCRIPTION: SEQ ID NO:16:

TTTTTGGATC CGGCTGGAAG ACTGAGCCTG GACC               34

(2) INFORMATION FOR SEQ ID NO:17:

(i) SEQUENCE CHARACTERISTICS:
        (A) LENGTH: 33 bases
        (B) TYPE: nucleic acid
        (C) STRANDEDNESS: single
        (D) TOPOLOGY: linear (xi) SEQUENCE DESCRIPTION: SEQ ID NO:17:

TTTTTGGATC CGCATGCCAG CTATGTGGTA GGG                33

(2) INFORMATION FOR SEQ ID NO:18:

(i) SEQUENCE CHARACTERISTICS:
        (A) LENGTH: 36 bases
        (B) TYPE: nucleic acid
        (C) STRANDEDNESS: single
        (D) TOPOLOGY: linear (xi) SEQUENCE DESCRIPTION: SEQ ID NO:18:

TTTTTGAATT CGGCAGACAA AGGGACAAGT GAGAAG                36

(2) INFORMATION FOR SEQ ID NO:19:

(i) SEQUENCE CHARACTERISTICS:
        (A) LENGTH: 32 bases
        (B) TYPE: nucleic acid
        (C) STRANDEDNESS: single
        (D) TOPOLOGY: linear (xi) SEQUENCE DESCRIPTION: SEQ ID NO:19:

TTTTTAAGCT TCAGCCCTGC GTGAACTGCA GG                    32

(2) INFORMATION FOR SEQ ID NO:20:

(i) SEQUENCE CHARACTERISTICS:
        (A) LENGTH: 33 bases
        (B) TYPE: nucleic acid
        (C) STRANDEDNESS: single
        (D) TOPOLOGY: linear (xi) SEQUENCE DESCRIPTION: SEQ ID NO:20:

TTTTTGAATT CGACTCAAGA GTGACCACTG GAG                   33

(2) INFORMATION FOR SEQ ID NO:21:

(i) SEQUENCE CHARACTERISTICS:
        (A) LENGTH: 34 bases
        (B) TYPE: nucleic acid
        (C) STRANDEDNESS: single
        (D) TOPOLOGY: linear (xi) SEQUENCE DESCRIPTION: SEQ ID NO:21:

TTTTTAAGCT TCCAAAGTGC ATGTCACATG CCAC                  34

(2) INFORMATION FOR SEQ ID NO:22:

(i) SEQUENCE CHARACTERISTICS:
        (A) LENGTH: 34 bases
        (B) TYPE: nucleic acid
        (C) STRANDEDNESS: single
        (D) TOPOLOGY: linear (xi) SEQUENCE DESCRIPTION: SEQ ID NO:22:

TTTTTGAATT CGAGGTCAGT GCAGCTCACT GAAC                  34

(2) INFORMATION FOR SEQ ID NO:23:

(i) SEQUENCE CHARACTERISTICS:
        (A) LENGTH: 33 bases
        (B) TYPE: nucleic acid
        (C) STRANDEDNESS: single
        (D) TOPOLOGY: linear (xi) SEQUENCE DESCRIPTION: SEQ ID NO:23:

TTTTAAGCTT CCACCATGGA ACCCCGACC GTC                    33

(2) INFORMATION FOR SEQ ID NO:24:

(i) SEQUENCE CHARACTERISTICS:
        (A) LENGTH: 24 bases
        (B) TYPE: nucleic acid
        (C) STRANDEDNESS: single
        (D) TOPOLOGY: linear (xi) SEQUENCE DESCRIPTION: SEQ ID NO:24:

TTTTGCGCTG CGGATCCGGA TGGG                                          24

(2) INFORMATION FOR SEQ ID NO:25:

(i) SEQUENCE CHARACTERISTICS:
        (A) LENGTH: 30 bases
        (B) TYPE: nucleic acid
        (C) STRANDEDNESS: single
        (D) TOPOLOGY: linear (xi) SEQUENCE DESCRIPTION: SEQ ID NO:25:

TTTTTGGATC CAGCCCATGT CCCAAATCAC                                    30

(2) INFORMATION FOR SEQ ID NO:26:

(i) SEQUENCE CHARACTERISTICS:
        (A) LENGTH: 30 bases
        (B) TYPE: nucleic acid
        (C) STRANDEDNESS: single
        (D) TOPOLOGY: linear (xi) SEQUENCE DESCRIPTION: SEQ ID NO:26:

TTTTTGAATT CCTCGAGCAC CGACTCATCG                                    30

(2) INFORMATION FOR SEQ ID NO:27:

(i) SEQUENCE CHARACTERISTICS:
        (A) LENGTH: 40 bases
        (B) TYPE: nucleic acid
        (C) STRANDEDNESS: single
        (D) TOPOLOGY: linear (xi) SEQUENCE DESCRIPTION: SEQ ID NO:27:

GCGCGCAAGC TTGCCACCAT GTCCCGGATC AGTGGCCTAC                         40

(2) INFORMATION FOR SEQ ID NO:28:

(i) SEQUENCE CHARACTERISTICS:
        (A) LENGTH: 28 bases
        (B) TYPE: nucleic acid
        (C) STRANDEDNESS: single
        (D) TOPOLOGY: linear (xi) SEQUENCE DESCRIPTION: SEQ ID NO:28:

GAACACAGCC TCGAGGGCGG GCGTAGCC                                      28

(2) INFORMATION FOR SEQ ID NO:29:

(i) SEQUENCE CHARACTERISTICS:
        (A) LENGTH: 33 bases
        (B) TYPE: nucleic acid
        (C) STRANDEDNESS: single
        (D) TOPOLOGY: linear (xi) SEQUENCE DESCRIPTION: SEQ ID NO:29:

GCGCGCAAGC TTCGCTTACC TGCCAGACTG CGC                                33

(2) INFORMATION FOR SEQ ID NO:30:

(i) SEQUENCE CHARACTERISTICS:
        (A) LENGTH: 33 bases
        (B) TYPE: nucleic acid
        (C) STRANDEDNESS: single
        (D) TOPOLOGY: linear (xi) SEQUENCE DESCRIPTION: SEQ ID NO:30:

-continued

```
GCGCGCGAAT TCTCTGTTTA GTGTTCTGTT GGG                                   33
```

(2) INFORMATION FOR SEQ ID NO:31:

(i) SEQUENCE CHARACTERISTICS:
        (A) LENGTH: 2153 base pairs
        (B) TYPE: nucleic acid
        (C) STRANDEDNESS: double
        (D) TOPOLOGY: linear (xi) SEQUENCE DESCRIPTION: SEQ ID NO:31:

```
TTCGACGTGA TCAGACCCAA CTCAGACCCG GTCATACTTG GACCGAATGC TGCCAAATCC      60

CCCACCTCTA CCCAGATCTG AGCCTACGCG GGGTGCCGAC CCAGCTCGTG GACGGGGATA     120

CGGTGACCTT TGACCCAAAA GTCTTGGCCG GGACCAGCCG GACACTGGCC CTCGGCCGGG     180

AGCTCCGAGT CTCAGGCGGT CCCGGTTGTC TTCCTGTCGG TGCCGCTTCC GCCTGCCCTT     240

CTTGAAAACC CACCCCCAGC TTTGACCTGG AAAATGGGCT CTCGTGTGGG AGGAGGGCCC     300

TGGACCCTCA GTCCAGCCCT GGCCTGGGCC GGATT ATG CAG GCT CCA GTC CCG        353
                                       Met Gln Ala Pro Val Pro
                                        1               5

CAC AGC CAG CGG CGC GAG TCC TTC CTG TAC CGC TCA GAT AGC GAC TAT       401
His Ser Gln Arg Arg Glu Ser Phe Leu Tyr Arg Ser Asp Ser Asp Tyr
            10                  15                  20

GAA CTC TCG CCC AAG GCC ATG TCT CGG AAC TCC TCT GTG GCC AGC GAC       449
Glu Leu Ser Pro Lys Ala Met Ser Arg Asn Ser Ser Val Ala Ser Asp
        25                  30                  35

CTA CAT GGA GAG GAC ATG ATT GTG ACG CCC TTT GCC CAG GTC CTG GCC       497
Leu His Gly Glu Asp Met Ile Val Thr Pro Phe Ala Gln Val Leu Ala
    40                  45                  50

AGT CTG CGG ACC GTT CGG AGC AAC GTG GCG GCC CTT GCC CGC CAG CAA       545
Ser Leu Arg Thr Val Arg Ser Asn Val Ala Ala Leu Ala Arg Gln Gln
55                  60                  65                  70

TGC CTA GGA GCA GCC AAG CAG GGA CCC GTC GGA AAC CCT TCA TCC AGC       593
Cys Leu Gly Ala Ala Lys Gln Gly Pro Val Gly Asn Pro Ser Ser Ser
                75                  80                  85

AAT CAG CTC CCT CCT GCA GAG GAC ACG GGG CAG AAG CTG GCA TTG GAG       641
Asn Gln Leu Pro Pro Ala Glu Asp Thr Gly Gln Lys Leu Ala Leu Glu
            90                  95                 100

ACG CTA GAC GAG CTG GAC TGG TGC CTG GAT CAG TTG GAG ACG CTG CAG       689
Thr Leu Asp Glu Leu Asp Trp Cys Leu Asp Gln Leu Glu Thr Leu Gln
        105                 110                 115

ACC CGG CAC TCG GTG GGG GAG ATG GCC TCC AAC AAG TTC AAG CGG ATC       737
Thr Arg His Ser Val Gly Glu Met Ala Ser Asn Lys Phe Lys Arg Ile
    120                 125                 130

CTG AAC CGG GAG TTG ACC CAC CTG TCC GAA ACC AGC CGC TCC GGG AAC       785
Leu Asn Arg Glu Leu Thr His Leu Ser Glu Thr Ser Arg Ser Gly Asn
135                 140                 145                 150

CAG GTG TCC GAG TAC ATC TCC CGG ACC TTC CTG GAC CAG CAG ACC GAG       833
Gln Val Ser Glu Tyr Ile Ser Arg Thr Phe Leu Asp Gln Gln Thr Glu
                155                 160                 165

GTG GAG CTG CCC AAG GTG ACC GCT GAG GAG GCC CCA CAG CCC ATG TCC       881
Val Glu Leu Pro Lys Val Thr Ala Glu Glu Ala Pro Gln Pro Met Ser
            170                 175                 180

CGG ATC AGT GGC TTA CAT GGG CTC TGC CAC AGT GCC AGC CTC TCC TCA       929
Arg Ile Ser Gly Leu His Gly Leu Cys His Ser Ala Ser Leu Ser Ser
        185                 190                 195

GCC ACT GTC CCA CGC TTT GGG GTC CAG ACT GAC CAG GAG GAG CAA CTG       977
Ala Thr Val Pro Arg Phe Gly Val Gln Thr Asp Gln Glu Glu Gln Leu
    200                 205                 210
```

-continued

| | | |
|---|---|---|
| GCC AAG GAG CTA GAA GAC ACC AAC AAG TGG GGA CTT GAT GTG TTC AAG<br>Ala Lys Glu Leu Glu Asp Thr Asn Lys Trp Gly Leu Asp Val Phe Lys<br>215                          220                          225                          230 | 1025 |
| GTG GCG GAG CTA AGT GGG AAC CAG CCC CTC ACA GCT ATC ATA TTC AGC<br>Val Ala Glu Leu Ser Gly Asn Gln Pro Leu Thr Ala Ile Ile Phe Ser<br>235                          240                          245 | 1073 |
| ATT TTT CAG GAG CGG GAC CTG CTG AAG ACA TTC CAG ATC CCA GCA GAC<br>Ile Phe Gln Glu Arg Asp Leu Leu Lys Thr Phe Gln Ile Pro Ala Asp<br>250                          255                          260 | 1121 |
| ACA CTG GCC ACC TAC CTG CTG ATG CTG GAG GGT CAC TAC CAC GCC AAT<br>Thr Leu Ala Thr Tyr Leu Leu Met Leu Glu Gly His Tyr His Ala Asn<br>265                          270                          275 | 1169 |
| GTG GCC TAC CAC AAC AGC CTA CAT GCC GCC GAC GTG GCC CAG TCC ACG<br>Val Ala Tyr His Asn Ser Leu His Ala Ala Asp Val Ala Gln Ser Thr<br>280                          285                          290 | 1217 |
| CAT GTG CTG CTG GCT ACG CCC GCC CTC GAG GCT GTG TTC ACA GAC TTG<br>His Val Leu Leu Ala Thr Pro Ala Leu Glu Ala Val Phe Thr Asp Leu<br>295                          300                          305                          310 | 1265 |
| GAA ATC CTG GCT GCC CTC TTT GCA AGC GCC ATC CAC GAC GTG GAC CAT<br>Glu Ile Leu Ala Ala Leu Phe Ala Ser Ala Ile His Asp Val Asp His<br>315                          320                          325 | 1313 |
| CCT GGG GTC TCC AAC CAG TTT CTG ATT AAC ACC AAC TCA GAG CTG GCG<br>Pro Gly Val Ser Asn Gln Phe Leu Ile Asn Thr Asn Ser Glu Leu Ala<br>330                          335                          340 | 1361 |
| CTT ATG TAC AAC GAC GCC TCG GTG CTG GAG AAC CAT CAC CTG GCT GTG<br>Leu Met Tyr Asn Asp Ala Ser Val Leu Glu Asn His His Leu Ala Val<br>345                          350                          355 | 1409 |
| GGC TTC AAG CTG CTG CAG GCA GAG AAC TGC GAT ATC TTC CAG AAC CTC<br>Gly Phe Lys Leu Leu Gln Ala Glu Asn Cys Asp Ile Phe Gln Asn Leu<br>360                          365                          370 | 1457 |
| AGC GCC AAG CAG CGA CTG AGT CTG CGC AGG ATG GTC ATT GAC ATG GTG<br>Ser Ala Lys Gln Arg Leu Ser Leu Arg Arg Met Val Ile Asp Met Val<br>375                          380                          385                          390 | 1505 |
| CTG GCC ACA GAC ATG TCC AAA CAC ATG AAC CTC CTG GCC GAC CTC AAG<br>Leu Ala Thr Asp Met Ser Lys His Met Asn Leu Leu Ala Asp Leu Lys<br>395                          400                          405 | 1553 |
| ACC ATG GTG GAG ACC AAG AAG GTG ACA AGC CTC GGT GTC CTC CTC CTG<br>Thr Met Val Glu Thr Lys Lys Val Thr Ser Leu Gly Val Leu Leu Leu<br>410                          415                          420 | 1601 |
| GAC AAC TAT TCC GAC CGA ATC CAG GTC TTG CAG AAC CTG GTG CAC TGT<br>Asp Asn Tyr Ser Asp Arg Ile Gln Val Leu Gln Asn Leu Val His Cys<br>425                          430                          435 | 1649 |
| GCT GAT CTG AGC AAC CCC ACC AAG CCG CTG CCC CTG TAC CGC CAG TGG<br>Ala Asp Leu Ser Asn Pro Thr Lys Pro Leu Pro Leu Tyr Arg Gln Trp<br>440                          445                          450 | 1697 |
| ACG GAC CGC ATC ATG GCC GAG TTC TTC CAG CAG GGA GAC CGC GAG CGT<br>Thr Asp Arg Ile Met Ala Glu Phe Phe Gln Gln Gly Asp Arg Glu Arg<br>455                          460                          465                          470 | 1745 |
| GAG TCG GGC CTG GAC ATC AGT CCC ATG TGT GAC AAG CAT ACG GCC TCA<br>Glu Ser Gly Leu Asp Ile Ser Pro Met Cys Asp Lys His Thr Ala Ser<br>475                          480                          485 | 1793 |
| GTG GAG AAG TCC CAG GTG GGT TTC ATT GAC TAC ATT GCT CAC CCA CTG<br>Val Glu Lys Ser Gln Val Gly Phe Ile Asp Tyr Ile Ala His Pro Leu<br>490                          495                          500 | 1841 |
| TGG GAG ACT TGG GCT GAC CTG GTC CAC CCA GAT GCA CAG GAC CTG CTG<br>Trp Glu Thr Trp Ala Asp Leu Val His Pro Asp Ala Gln Asp Leu Leu<br>505                          510                          515 | 1889 |
| GAC ACG CTG GAG GAC AAT CGA GAG TGG TAC CAG AGC AAG ATC CCC CGA<br>Asp Thr Leu Glu Asp Asn Arg Glu Trp Tyr Gln Ser Lys Ile Pro Arg<br>520                          525                          530 | 1937 |

```
AGT CCC TCA GAC CTC ACC AAC CCC GAG CGG GAC GGG CCT GAC AGA TTC      1985
Ser Pro Ser Asp Leu Thr Asn Pro Glu Arg Asp Gly Pro Asp Arg Phe
535                 540                 545                 550

CAG TTT GAA CTG ACT CTG GAG GAG GCA GAG GAA GAG GAT GAG GAG GAA      2033
Gln Phe Glu Leu Thr Leu Glu Glu Ala Glu Glu Glu Asp Glu Glu Glu
                555                 560                 565

GAA GAG GAG GGG GAA GAG ACA GCT TTA GCC AAA GAG GCC TTG GAG TTG      2081
Glu Glu Glu Gly Glu Glu Thr Ala Leu Ala Lys Glu Ala Leu Glu Leu
            570                 575                 580

CCT GAC ACT GAA CTC CTG TCC CCT GAA GCC GGC CCA GCC CCT GGG GAC      2129
Pro Asp Thr Glu Leu Leu Ser Pro Glu Ala Gly Pro Ala Pro Gly Asp
        585                 590                 595

TTA CCC CTC GAC AAC CAG AGG ACT                                      2153
Leu Pro Leu Asp Asn Gln Arg Thr
    600                 605

(2) INFORMATION FOR SEQ ID NO:32:

(i) SEQUENCE CHARACTERISTICS:
        (A) LENGTH: 606 amino acids
        (B) TYPE: amino acid
        (D) TOPOLOGY: unknown (xi) SEQUENCE DESCRIPTION: SEQ ID NO:32:

Met Gln Ala Pro Val Pro His Ser Gln Arg Arg Glu Ser Phe Leu Tyr
 1               5                  10                  15

Arg Ser Asp Ser Asp Tyr Glu Leu Ser Pro Lys Ala Met Ser Arg Asn
            20                  25                  30

Ser Ser Val Ala Ser Asp Leu His Gly Glu Asp Met Ile Val Thr Pro
        35                  40                  45

Phe Ala Gln Val Leu Ala Ser Leu Arg Thr Val Arg Ser Asn Val Ala
    50                  55                  60

Ala Leu Ala Arg Gln Gln Cys Leu Gly Ala Ala Lys Gln Gly Pro Val
65                  70                  75                  80

Gly Asn Pro Ser Ser Ser Asn Gln Leu Pro Pro Ala Glu Asp Thr Gly
                85                  90                  95

Gln Lys Leu Ala Leu Glu Thr Leu Asp Glu Leu Asp Trp Cys Leu Asp
            100                 105                 110

Gln Leu Glu Thr Leu Gln Thr Arg His Ser Val Gly Glu Met Ala Ser
        115                 120                 125

Asn Lys Phe Lys Arg Ile Leu Asn Arg Glu Leu Thr His Leu Ser Glu
    130                 135                 140

Thr Ser Arg Ser Gly Asn Gln Val Ser Glu Tyr Ile Ser Arg Thr Phe
145                 150                 155                 160

Leu Asp Gln Gln Thr Glu Val Glu Leu Pro Lys Val Thr Ala Glu Glu
                165                 170                 175

Ala Pro Gln Pro Met Ser Arg Ile Ser Gly Leu His Gly Leu Cys His
            180                 185                 190

Ser Ala Ser Leu Ser Ser Ala Thr Val Pro Arg Phe Gly Val Gln Thr
        195                 200                 205

Asp Gln Glu Glu Gln Leu Ala Lys Glu Leu Glu Asp Thr Asn Lys Trp
    210                 215                 220

Gly Leu Asp Val Phe Lys Val Ala Glu Leu Ser Gly Asn Gln Pro Leu
225                 230                 235                 240

Thr Ala Ile Ile Phe Ser Ile Phe Gln Glu Arg Asp Leu Leu Lys Thr
                245                 250                 255
```

```
Phe Gln Ile Pro Ala Asp Thr Leu Ala Thr Tyr Leu Met Leu Glu
            260                 265                 270

Gly His Tyr His Ala Asn Val Ala Tyr His Asn Ser Leu His Ala Ala
        275                 280                 285

Asp Val Ala Gln Ser Thr His Val Leu Leu Ala Thr Pro Ala Leu Glu
    290                 295                 300

Ala Val Phe Thr Asp Leu Glu Ile Leu Ala Ala Leu Phe Ala Ser Ala
305                 310                 315                 320

Ile His Asp Val Asp His Pro Gly Val Ser Asn Gln Phe Leu Ile Asn
                325                 330                 335

Thr Asn Ser Glu Leu Ala Leu Met Tyr Asn Asp Ala Ser Val Leu Glu
            340                 345                 350

Asn His His Leu Ala Val Gly Phe Lys Leu Leu Gln Ala Glu Asn Cys
        355                 360                 365

Asp Ile Phe Gln Asn Leu Ser Ala Lys Gln Arg Leu Ser Leu Arg Arg
    370                 375                 380

Met Val Ile Asp Met Val Leu Ala Thr Asp Met Ser Lys His Met Asn
385                 390                 395                 400

Leu Leu Ala Asp Leu Lys Thr Met Val Glu Thr Lys Lys Val Thr Ser
                405                 410                 415

Leu Gly Val Leu Leu Leu Asp Asn Tyr Ser Asp Arg Ile Gln Val Leu
            420                 425                 430

Gln Asn Leu Val His Cys Ala Asp Leu Ser Asn Pro Thr Lys Pro Leu
        435                 440                 445

Pro Leu Tyr Arg Gln Trp Thr Asp Arg Ile Met Ala Glu Phe Phe Gln
    450                 455                 460

Gln Gly Asp Arg Glu Arg Glu Ser Gly Leu Asp Ile Ser Pro Met Cys
465                 470                 475                 480

Asp Lys His Thr Ala Ser Val Glu Lys Ser Gln Val Gly Phe Ile Asp
                485                 490                 495

Tyr Ile Ala His Pro Leu Trp Glu Thr Trp Ala Asp Leu Val His Pro
            500                 505                 510

Asp Ala Gln Asp Leu Leu Asp Thr Leu Glu Asp Asn Arg Glu Trp Tyr
        515                 520                 525

Gln Ser Lys Ile Pro Arg Ser Pro Ser Asp Leu Thr Asn Pro Glu Arg
    530                 535                 540

Asp Gly Pro Asp Arg Phe Gln Phe Glu Leu Thr Leu Glu Glu Ala Glu
545                 550                 555                 560

Glu Glu Asp Glu Glu Glu Glu Glu Gly Glu Glu Thr Ala Leu Ala
                565                 570                 575

Lys Glu Ala Leu Glu Leu Pro Asp Thr Glu Leu Leu Ser Pro Glu Ala
            580                 585                 590

Gly Pro Ala Pro Gly Asp Leu Pro Leu Asp Asn Gln Arg Thr
        595                 600                 605

(2) INFORMATION FOR SEQ ID NO:33:

(i) SEQUENCE CHARACTERISTICS:
        (A) LENGTH: 885 amino acids
        (B) TYPE: amino acid
        (D) TOPOLOGY: unknown (xi) SEQUENCE DESCRIPTION: SEQ ID NO:33:

Met Glu Pro Pro Thr Val Pro Ser Glu Arg Ser Leu Ser Leu Ser Leu
1               5                   10                  15
```

-continued

```
Pro Gly Pro Arg Glu Gly Gln Ala Thr Leu Lys Pro Pro Gln His
            20                  25                  30

Leu Trp Arg Gln Pro Arg Thr Pro Ile Arg Ile Gln Arg Gly Tyr
         35                  40                  45

Ser Asp Ser Ala Glu Arg Ala Glu Arg Glu Arg Gln Pro His Arg Pro
 50              55                  60

Ile Glu Arg Ala Asp Ala Met Asp Thr Ser Asp Arg Pro Gly Leu Arg
 65              70                  75                  80

Thr Thr Arg Met Ser Trp Pro Ser Ser Phe His Gly Thr Gly Thr Gly
                 85                  90                  95

Ser Gly Gly Ala Gly Gly Ser Ser Arg Arg Phe Glu Ala Glu Asn
            100                 105                 110

Gly Thr Ser Ala Gly Arg Ser Pro Leu Asp Pro Met Thr Ser Pro Ser
            115                 120                 125

Pro Gly Leu Val Leu His Ala Gly Ala Ala Thr Ser Gln Arg Arg Glu
            130                 135                 140

Ser Phe Leu Tyr Arg Ser Asp Ser Asp Tyr Asp Met Ser Pro Lys Thr
145                 150                 155                 160

Met Ser Arg Asn Ser Ser Val Thr Ser Glu Ala His Ala Glu Asp Leu
                165                 170                 175

Ile Val Thr Pro Phe Ala Gln Val Leu Ala Ser Leu Arg Ser Val Arg
            180                 185                 190

Ser Asn Phe Ser Leu Leu Thr Asn Val Pro Val Pro Ser Asn Lys Arg
            195                 200                 205

Ser Pro Leu Gly Gly Pro Thr Pro Val Cys Lys Ala Thr Leu Ser Glu
    210                 215                 220

Glu Thr Cys Gln Gln Leu Ala Arg Glu Thr Leu Glu Glu Leu Asp Trp
225                 230                 235                 240

Cys Leu Glu Gln Leu Glu Thr Met Gln Thr Tyr Arg Ser Val Ser Glu
                245                 250                 255

Met Ala Ser His Lys Phe Lys Arg Met Leu Asn Arg Glu Leu Thr His
            260                 265                 270

Leu Ser Glu Met Ser Arg Ser Gly Asn Gln Val Ser Glu Tyr Ile Ser
    275                 280                 285

Thr Thr Phe Leu Asp Lys Gln Asn Glu Val Glu Ile Pro Ser Pro Thr
    290                 295                 300

Met Lys Glu Arg Glu Lys Gln Gln Ala Pro Arg Pro Arg Pro Ser Pro
305                 310                 315                 320

Pro Pro Pro Pro Val Pro His Leu Gln Pro Met Ser Gln Ile Thr Gly
                325                 330                 335

Leu Lys Lys Leu Met His Ser Asn Ser Leu Asn Asn Ser Asn Ile Pro
            340                 345                 350

Arg Phe Gly Val Lys Thr Asp Gln Glu Glu Leu Leu Ala Gln Glu Leu
            355                 360                 365

Glu Asn Leu Asn Lys Trp Gly Leu Asn Ile Phe Cys Val Ser Asp Tyr
    370                 375                 380

Ala Gly Gly Arg Ser Leu Thr Cys Ile Met Tyr Met Ile Phe Gln Glu
385                 390                 395                 400

Arg Asp Leu Leu Lys Lys Phe Arg Ile Pro Val Asp Thr Met Val Thr
                405                 410                 415

Tyr Met Leu Thr Leu Glu Asp His Tyr His Ala Asp Val Ala Tyr His
            420                 425                 430

Asn Ser Leu His Ala Ala Asp Val Leu Gln Ser Thr His Val Leu Leu
```

-continued

```
                435                 440                 445
Ala Thr Pro Ala Leu Asp Ala Val Phe Thr Asp Leu Glu Ile Leu Ala
    450                 455                 460
Ala Leu Phe Ala Ala Ala Ile His Asp Val Asp His Pro Gly Val Ser
465                 470                 475                 480
Asn Gln Phe Leu Ile Asn Thr Asn Ser Glu Leu Ala Leu Met Tyr Asn
                485                 490                 495
Asp Glu Ser Val Leu Glu Asn His His Leu Ala Val Gly Phe Lys Leu
            500                 505                 510
Leu Gln Glu Glu Asn Cys Asp Ile Phe Gln Asn Leu Ser Lys Arg Gln
        515                 520                 525
Arg Gln Ser Leu Arg Lys Met Val Ile Asp Met Val Leu Ala Thr Asp
    530                 535                 540
Met Ser Lys His Met Thr Leu Leu Ala Asp Leu Lys Thr Met Val Glu
545                 550                 555                 560
Thr Lys Lys Val Thr Ser Ser Gly Val Leu Leu Leu Asp Asn Tyr Ser
                565                 570                 575
Asp Arg Ile Gln Val Leu Arg Asn Met Val His Cys Ala Asp Leu Ser
            580                 585                 590
Asn Pro Thr Lys Pro Leu Glu Leu Tyr Arg Gln Trp Thr Asp Arg Ile
        595                 600                 605
Met Ala Glu Phe Phe Gln Gln Gly Asp Arg Glu Arg Glu Arg Gly Met
    610                 615                 620
Glu Ile Ser Pro Met Cys Asp Lys His Thr Ala Ser Val Glu Lys Ser
625                 630                 635                 640
Gln Val Gly Phe Ile Asp Tyr Ile Val His Pro Leu Trp Glu Thr Trp
                645                 650                 655
Ala Asp Leu Val His Pro Asp Ala Gln Glu Ile Leu Asp Thr Leu Glu
            660                 665                 670
Asp Asn Arg Asp Trp Tyr Tyr Ser Ala Ile Arg Gln Ser Pro Ser Pro
        675                 680                 685
Pro Pro Glu Glu Glu Ser Arg Gly Pro Gly His Pro Pro Leu Pro Asp
    690                 695                 700
Lys Phe Gln Phe Glu Leu Thr Leu Glu Glu Glu Glu Glu Glu Glu Ile
705                 710                 715                 720
Ser Arg Ala Gln Ile Arg Cys Thr Ala Gln Glu Ala Leu Thr Glu Gln
                725                 730                 735
Gly Leu Ser Gly Val Glu Glu Ala Leu Asp Ala Thr Ile Ala Trp Glu
            740                 745                 750
Ala Ser Pro Ala Gln Glu Ser Leu Glu Val Met Ala Gln Glu Ala Ser
        755                 760                 765
Leu Glu Ala Glu Leu Glu Ala Val Tyr Leu Thr Gln Gln Ala Gln Ser
    770                 775                 780
Thr Gly Ser Glu Pro Val Ala Pro Asp Glu Phe Ser Asn Arg Glu Glu
785                 790                 795                 800
Phe Val Val Ala Val Ser His Ser Ser Pro Ser Ala Leu Ala Leu Gln
                805                 810                 815
Ser Pro Leu Leu Pro Ala Trp Arg Thr Leu Ser Val Ser Glu His Ala
            820                 825                 830
Pro Gly Leu Pro Gly Leu Pro Ser Thr Ala Ala Glu Val Glu Ala Gln
        835                 840                 845
Arg Glu His Gln Ala Ala Lys Arg Ala Cys Ser Ala Cys Ala Gly Thr
    850                 855                 860
```

-continued

```
Phe Gly Glu Asp Thr Ser Ala Leu Pro Ala Pro Gly Gly Gly Ser
865                 870                 875                 880

Gly Gly Asp Pro Thr
                885
```

(2) INFORMATION FOR SEQ ID NO:34:

(i) SEQUENCE CHARACTERISTICS:
        (A) LENGTH: 564 amino acids
        (B) TYPE: amino acid
        (D) TOPOLOGY: unknown (xi) SEQUENCE DESCRIPTION: SEQ ID NO:34:

```
Met Lys Glu His Gly Gly Thr Phe Ser Ser Thr Gly Ile Ser Gly Gly
1               5                   10                  15

Ser Gly Asp Ser Ala Met Asp Ser Leu Gln Pro Leu Gln Pro Asn Tyr
                20                  25                  30

Met Pro Val Cys Leu Phe Ala Glu Glu Ser Tyr Gln Lys Leu Ala Met
                35                  40                  45

Glu Thr Leu Glu Glu Leu Asp Trp Cys Leu Asp Gln Leu Glu Thr Ile
    50                  55                  60

Gln Thr Tyr Arg Ser Val Ser Glu Met Ala Ser Asn Lys Phe Lys Arg
65                  70                  75                  80

Met Leu Asn Arg Glu Leu Thr His Leu Ser Glu Met Ser Arg Ser Gly
                85                  90                  95

Asn Gln Val Ser Glu Val Ile Ser Asn Thr Phe Leu Asp Lys Gln Asn
                100                 105                 110

Asp Val Glu Ile Pro Ser Pro Thr Gln Lys Asp Arg Glu Lys Lys Lys
                115                 120                 125

Lys Gln Gln Leu Met Thr Gln Ile Ser Gly Val Lys Lys Leu Met His
130                 135                 140

Ser Ser Ser Leu Asn Asn Thr Ser Ile Ser Arg Phe Gly Val Asn Thr
145                 150                 155                 160

Glu Asn Glu Asp His Leu Ala Lys Glu Leu Glu Asp Leu Asn Lys Trp
                165                 170                 175

Gly Leu Asn Ile Phe Asn Val Ala Gly Tyr Ser His Asn Arg Pro Leu
                180                 185                 190

Thr Cys Ile Met Tyr Ala Ile Phe Gln Glu Arg Asp Leu Leu Lys Thr
                195                 200                 205

Phe Arg Ile Ser Ser Asp Thr Phe Ile Thr Tyr Met Met Thr Leu Glu
210                 215                 220

Asp His Tyr His Ser Asp Val Ala Tyr His Asn Ser Leu His Ala Ala
225                 230                 235                 240

Asp Val Ala Gln Ser Thr His Val Leu Leu Ser Thr Pro Ala Leu Asp
                245                 250                 255

Ala Val Phe Thr Asp Leu Glu Ile Leu Ala Ala Ile Phe Ala Ala Ala
                260                 265                 270

Ile His Asp Val Asp His Pro Gly Val Ser Asn Gln Phe Leu Ile Asn
                275                 280                 285

Thr Asn Ser Glu Leu Ala Leu Met Tyr Asn Asp Glu Ser Val Leu Glu
                290                 295                 300

Asn His His Leu Ala Val Gly Phe Lys Leu Leu Gln Glu Glu His Cys
305                 310                 315                 320

Asp Ile Phe Met Asn Leu Thr Lys Lys Gln Arg Gln Thr Leu Arg Lys
                325                 330                 335
```

-continued

```
Met Val Ile Asp Met Val Leu Ala Thr Asp Met Ser Lys His Met Ser
              340                 345                 350

Leu Leu Ala Asp Leu Lys Thr Met Val Glu Thr Lys Lys Val Thr Ser
              355                 360                 365

Ser Gly Val Leu Leu Asp Asn Tyr Thr Asp Arg Ile Gln Val Leu
              370                 375                 380

Arg Asn Met Val His Cys Ala Asp Leu Ser Asn Pro Thr Lys Ser Leu
385                 390                 395                 400

Glu Leu Tyr Arg Gln Trp Thr Asp Arg Ile Met Glu Glu Phe Phe Gln
              405                 410                 415

Gln Gly Asp Lys Glu Arg Glu Arg Gly Met Glu Ile Ser Pro Met Cys
              420                 425                 430

Asp Lys His Thr Ala Ser Val Glu Lys Ser Gln Val Gly Phe Ile Asp
              435                 440                 445

Tyr Ile Val His Pro Leu Trp Glu Thr Trp Ala Asp Leu Val Gln Pro
              450                 455                 460

Asp Ala Gln Asp Ile Leu Asp Thr Leu Glu Asp Asn Arg Asn Trp Tyr
465                 470                 475                 480

Gln Ser Met Ile Pro Gln Ser Pro Ser Pro Pro Leu Asp Glu Gln Asn
              485                 490                 495

Arg Asp Cys Gln Gly Leu Met Glu Lys Phe Gln Phe Glu Leu Thr Leu
              500                 505                 510

Asp Glu Glu Asp Ser Glu Gly Pro Glu Lys Glu Gly Glu Gly His Ser
              515                 520                 525

Tyr Phe Ser Ser Thr Lys Thr Leu Cys Val Ile Asp Pro Glu Asn Arg
              530                 535                 540

Asp Ser Leu Gly Glu Thr Asp Ile Asp Ile Ala Thr Glu Asp Lys Ser
545                 550                 555                 560

Pro Val Asp Thr (2) INFORMATION FOR SEQ ID NO:35:

(i) SEQUENCE CHARACTERISTICS:
            (A) LENGTH: 673 amino acids
            (B) TYPE: amino acid
            (D) TOPOLOGY: unknown (xi) SEQUENCE DESCRIPTION: SEQ ID NO:35:

Met Met His Val Asn Asn Phe Pro Phe Arg Arg His Ser Trp Ile Cys
1               5                  10                  15

Phe Asp Val Asp Asn Gly Thr Ser Ala Gly Arg Ser Pro Leu Asp Pro
              20                  25                  30

Met Thr Ser Pro Gly Ser Gly Leu Ile Leu Gln Ala Asn Phe Val His
              35                  40                  45

Ser Gln Arg Arg Glu Ser Phe Leu Tyr Arg Ser Asp Ser Asp Tyr Asp
              50                  55                  60

Leu Ser Pro Lys Ser Met Ser Arg Asn Ser Ser Ile Ala Ser Asp Ile
65                  70                  75                  80

His Gly Asp Asp Leu Ile Val Thr Pro Phe Ala Gln Val Leu Ala Ser
              85                  90                  95

Leu Arg Thr Val Arg Asn Asn Phe Ala Ala Leu Thr Asn Leu Gln Asp
              100                 105                 110

Arg Ala Pro Ser Lys Arg Ser Pro Met Cys Asn Gln Pro Ser Ile Asn
              115                 120                 125
```

```
Lys Ala Thr Ile Thr Glu Glu Ala Tyr Gln Lys Leu Ala Ser Glu Thr
    130                 135                 140

Leu Glu Glu Leu Asp Trp Cys Leu Asp Gln Leu Glu Thr Leu Gln Thr
145                 150                 155                 160

Arg His Ser Val Ser Glu Met Ala Ser Asn Lys Phe Lys Arg Met Leu
                165                 170                 175

Asn Arg Glu Leu Thr His Leu Ser Glu Met Ser Arg Ser Gly Asn Gln
            180                 185                 190

Val Ser Glu Phe Ile Ser Asn Thr Phe Leu Asp Lys Gln His Glu Val
        195                 200                 205

Glu Ile Pro Ser Pro Thr Gln Lys Glu Lys Glu Lys Lys Lys Arg Pro
    210                 215                 220

Met Ser Gln Ile Ser Gly Val Lys Lys Leu Met His Ser Ser Ser Leu
225                 230                 235                 240

Thr Asn Ser Ser Ile Pro Arg Phe Gly Val Lys Thr Glu Gln Glu Asp
                245                 250                 255

Val Leu Ala Lys Glu Leu Glu Asp Val Asn Lys Trp Gly Leu His Val
            260                 265                 270

Phe Arg Ile Ala Glu Leu Ser Gly Asn Arg Pro Leu Thr Val Ile Met
        275                 280                 285

His Thr Ile Phe Gln Glu Arg Asp Leu Leu Lys Thr Phe Lys Ile Pro
    290                 295                 300

Val Asp Thr Leu Ile Thr Tyr Leu Met Thr Leu Glu Asp His Tyr His
305                 310                 315                 320

Ala Asp Val Ala Tyr His Asn Asn Ile His Ala Ala Asp Val Val Gln
                325                 330                 335

Ser Thr His Val Leu Leu Ser Thr Pro Ala Leu Glu Ala Val Phe Thr
            340                 345                 350

Asp Leu Glu Ile Leu Ala Ala Ile Phe Ala Ser Ala Ile His Asp Val
        355                 360                 365

Asp His Pro Gly Val Ser Asn Gln Phe Leu Ile Asn Thr Asn Ser Glu
    370                 375                 380

Leu Ala Leu Met Tyr Asn Asp Ser Ser Val Leu Glu Asn His His Leu
385                 390                 395                 400

Ala Val Gly Phe Lys Leu Leu Gln Glu Glu Asn Cys Asp Ile Phe Gln
                405                 410                 415

Asn Leu Thr Lys Lys Gln Arg Gln Ser Leu Arg Lys Met Val Ile Asp
            420                 425                 430

Ile Val Leu Ala Thr Asp Met Ser Lys His Met Asn Leu Leu Ala Asp
        435                 440                 445

Leu Lys Thr Met Val Glu Thr Lys Lys Val Thr Ser Ser Gly Val Leu
    450                 455                 460

Leu Leu Asp Asn Tyr Ser Asp Arg Ile Gln Val Leu Gln Asn Met Val
465                 470                 475                 480

His Cys Ala Asp Leu Ser Asn Pro Thr Lys Pro Leu Gln Leu Tyr Arg
                485                 490                 495

Gln Trp Thr Asp Arg Ile Met Glu Glu Phe Phe Arg Gln Gly Asp Arg
            500                 505                 510

Glu Arg Glu Arg Gly Met Glu Ile Ser Pro Met Cys Asp Lys His Asn
        515                 520                 525

Ala Ser Val Glu Lys Ser Gln Val Gly Phe Ile Asp Tyr Ile Val His
    530                 535                 540

Pro Leu Trp Glu Thr Trp Ala Asp Leu Val His Pro Asp Ala Gln Asp
```

```
545             550             555             560
Ile Leu Asp Thr Leu Glu Asp Asn Arg Glu Trp Tyr Gln Ser Thr Ile
                565                 570             575

Pro Gln Ser Pro Ser Pro Ala Pro Asp Asp Pro Glu Glu Gly Arg Gln
            580             585                 590

Gly Gln Thr Gly Lys Phe Gln Phe Glu Leu Thr Leu Glu Glu Asp Gly
            595             600             605

Glu Ser Asp Thr Glu Lys Asp Ser Gly Ser Gln Val Glu Glu Asp Thr
            610             615             620

Ser Cys Ser Asp Ser Lys Thr Leu Cys Thr Gln Asp Ser Glu Ser Thr
625             630             635             640

Glu Ile Pro Leu Asp Glu Gln Val Glu Glu Ala Val Gly Glu Glu
                645             650             655

Glu Glu Ser Gln Pro Glu Ala Cys Val Ile Asp Asp Arg Ser Pro Asp
            660             665             670

Thr (2) INFORMATION FOR SEQ ID NO:36:

(i) SEQUENCE CHARACTERISTICS:
        (A) LENGTH: 336 base pairs
        (B) TYPE: nucleic acid
        (C) STRANDEDNESS: double
        (D) TOPOLOGY: linear (xi) SEQUENCE DESCRIPTION: SEQ ID NO:36:

GCT GTC CAG AAA AGG TCC CGC GCA GTC GGC GCT CGG TCC AGC CTC CAC        48
Ala Val Gln Lys Arg Ser Arg Ala Val Gly Ala Arg Ser Ser Leu His
            5                   10                  15

GCA GTC CTG GCG ATG CAG GGC CCC CCC GCG CCC GCC CCG GTC CCC GGG        96
Ala Val Leu Ala Met Gln Gly Pro Pro Ala Pro Ala Pro Val Pro Gly
            20                  25                  30

CCC GGC TCC CCT CGG GGA TCC CCG CGC GGC TCC CCC GGG CTC TTC AGG       144
Pro Gly Ser Pro Arg Gly Ser Pro Arg Gly Ser Pro Gly Leu Phe Arg
            35                  40                  45

AAG CTT TTG GTG AAT CAG AGC ATC CGC CTG CAG CGG CGC TTC ACG GTG       192
Lys Leu Leu Val Asn Gln Ser Ile Arg Leu Gln Arg Arg Phe Thr Val
        50                  55                  60

GCC CAT CCG CTG TGC TTT GAC CTG GAA AAT GGG CTC TCG TGT GGG AGG       240
Ala His Pro Leu Cys Phe Asp Leu Glu Asn Gly Leu Ser Cys Gly Arg
65                  70                  75                  80

AGG GCC CTG GAC CCT CAG TCC AGC CCT GGC CTG GGC CGG ATT ATG CAG       288
Arg Ala Leu Asp Pro Gln Ser Ser Pro Gly Leu Gly Arg Ile Met Gln
                85                  90                  95

GCT CCA GTC CCG CAC AGC CAG CGG CGC GAG TCC TTC CTG TAC CGC TCA       336
Ala Pro Val Pro His Ser Gln Arg Arg Glu Ser Phe Leu Tyr Arg Ser
            100                 105                 110

(2) INFORMATION FOR SEQ ID NO:37:

(i) SEQUENCE CHARACTERISTICS:
        (A) LENGTH: 112 amino acids
        (B) TYPE: amino acid
        (D) TOPOLOGY: unknown (xi) SEQUENCE DESCRIPTION: SEQ ID NO:37:

Ala Val Gln Lys Arg Ser Arg Ala Val Gly Ala Arg Ser Ser Leu His
1               5                   10                  15

Ala Val Leu Ala Met Gln Gly Pro Pro Ala Pro Ala Pro Val Pro Gly
            20                  25                  30
```

```
Pro Gly Ser Pro Arg Gly Ser Pro Arg Gly Ser Pro Gly Leu Phe Arg
            35                  40                  45

Lys Leu Leu Val Asn Gln Ser Ile Arg Leu Gln Arg Arg Phe Thr Val
 50                      55                  60

Ala His Pro Leu Cys Phe Asp Leu Glu Asn Gly Leu Ser Cys Gly Arg
 65                  70                  75                  80

Arg Ala Leu Asp Pro Gln Ser Ser Pro Gly Leu Gly Arg Ile Met Gln
                 85                  90                  95

Ala Pro Val Pro His Ser Gln Arg Glu Ser Phe Leu Tyr Arg Ser
                100                 105                 110
```

(2) INFORMATION FOR SEQ ID NO:38:

(i) SEQUENCE CHARACTERISTICS:
        (A) LENGTH: 438 amino acids
        (B) TYPE: amino acid
        (D) TOPOLOGY: unknown (xi) SEQUENCE DESCRIPTION: SEQ ID NO:38:

```
Glu Thr Leu Glu Glu Leu Asp Trp Cys Leu Glu Gln Leu Glu Thr Leu
  1               5                  10                  15

Gln Thr Arg Arg Ser Val Gly Glu Met Ala Ser Asn Lys Phe Lys Arg
             20                  25                  30

Met Leu Asn Arg Glu Leu Thr His Leu Ser Glu Thr Ser Arg Ser Gly
             35                  40                  45

Asn Gln Val Ser Glu Tyr Ile Ser Gln Thr Phe Leu Asp Gln Gln Ala
 50                      55                  60

Glu Val Glu Leu Pro Ala Leu Arg Lys Ser Cys His Thr Thr Ala Ala
 65                  70                  75                  80

Ile Pro Arg Phe Gly Val Gln Thr Asp Gln Glu Glu Gln Leu Ala Lys
                 85                  90                  95

Glu Leu Glu Asp Thr Asn Lys Trp Gly Leu Asp Val Phe Lys Val Ala
                100                 105                 110

Glu Leu Ser Gly Asn Arg Pro Leu Thr Ala Val Ile Phe Arg Val Leu
            115                 120                 125

Gln Glu Arg Asp Leu Leu Lys Thr Phe Gln Ile Pro Ala Asp Thr Leu
130                 135                 140

Leu Arg Tyr Leu Leu Thr Leu Glu Gly His Tyr His Ser Asn Val Ala
145                 150                 155                 160

Tyr His Asn Ser Ile His Ala Ala Asp Val Val Gln Ser Ala His Val
                165                 170                 175

Leu Leu Gly Thr Pro Ala Leu Glu Ala Val Phe Thr Asp Leu Glu Val
            180                 185                 190

Leu Ala Ala Ile Phe Ala Cys Ala Ile His Asp Val Asp His Pro Gly
            195                 200                 205

Val Ser Asn Gln Phe Leu Ile Asn Thr Asn Ser Glu Leu Ala Leu Met
    210                 215                 220

Tyr Asn Asp Ser Ser Val Leu Glu Asn His His Leu Ala Val Gly Phe
225                 230                 235                 240

Lys Leu Leu Gln Gly Glu Asn Cys Asp Ile Phe Gln Asn Leu Ser Thr
                245                 250                 255

Lys Gln Lys Leu Ser Leu Arg Arg Met Val Ile Asp Met Val Leu Ala
            260                 265                 270

Thr Asp Met Ser Lys His Met Ser Leu Leu Ala Asp Leu Lys Thr Met
            275                 280                 285
```

```
Val Glu Thr Lys Lys Val Thr Ser Leu Gly Val Leu Leu Asp Asn
    290                 295                 300

Tyr Ser Asp Arg Ile Gln Val Leu Gln Ser Leu Val His Cys Ala Asp
305                 310                 315                 320

Leu Ser Asn Pro Ala Lys Pro Leu Pro Leu Tyr Arg Gln Trp Thr Glu
                325                 330                 335

Arg Ile Met Ala Glu Phe Phe Gln Gln Gly Asp Arg Glu Arg Glu Ser
                340                 345                 350

Gly Leu Asp Ile Ser Pro Met Cys Asp Lys His Thr Ala Ser Val Glu
                355                 360                 365

Lys Ser Gln Val Gly Phe Ile Asp Tyr Ile Ala His Pro Leu Trp Glu
    370                 375                 380

Thr Trp Ala Asp Leu Val His Pro Asp Ala Gln Glu Leu Leu Asp Thr
385                 390                 395                 400

Leu Glu Asp Asn Arg Glu Trp Tyr Gln Ser Arg Val Pro Pro Glu Arg
                405                 410                 415

Asp Gly Pro Asp Arg Phe Gln Phe Glu Leu Thr Leu Glu Glu Ala Glu
                420                 425                 430

Glu Glu Asp Glu Glu Glu
            435

(2) INFORMATION FOR SEQ ID NO:39:

(i) SEQUENCE CHARACTERISTICS:
        (A) LENGTH: 10 amino acids
        (B) TYPE: amino acid
        (D) TOPOLOGY: unknown (xi) SEQUENCE DESCRIPTION: SEQ ID NO:39:

Met Glu Thr Leu Glu Glu Leu Asp Trp Cys
1               5                   10

(2) INFORMATION FOR SEQ ID NO:40:

(i) SEQUENCE CHARACTERISTICS:
        (A) LENGTH: 501 amino acids
        (B) TYPE: amino acid
        (D) TOPOLOGY: unknown (xi) SEQUENCE DESCRIPTION: SEQ ID NO:40:

Glu Thr Leu Glu Glu Leu Asp Trp Cys Leu Asp Gln Leu Glu Thr Leu
1               5                   10                  15

Gln Thr Arg His Ser Val Gly Glu Met Ala Ser Asn Lys Phe Lys Arg
                20                  25                  30

Ile Leu Asn Arg Glu Leu Thr His Leu Ser Glu Thr Ser Arg Ser Gly
                35                  40                  45

Asn Gln Val Ser Glu Tyr Ile Ser Arg Thr Phe Leu Asp Gln Gln Thr
    50                  55                  60

Glu Val Glu Leu Pro Lys Val Thr Ala Glu Glu Ala Pro Gln Pro Met
65                  70                  75                  80

Ser Arg Ile Ser Gly Leu His Gly Leu Cys His Ser Ser Ala Thr Val
                85                  90                  95

Pro Arg Phe Gly Val Gln Thr Asp Gln Glu Glu Gln Leu Ala Lys Glu
                100                 105                 110

Leu Glu Asp Thr Asn Lys Trp Gly Leu Asp Val Phe Lys Val Ala Glu
                115                 120                 125

Leu Ser Gly Asn Gln Pro Leu Thr Ala Ile Ile Phe Ser Ile Phe Gln
```

-continued

```
              130                 135                 140
Glu Arg Asp Leu Leu Lys Thr Phe Gln Ile Pro Ala Asp Thr Leu Ala
145                 150                 155                 160
Thr Tyr Leu Leu Met Leu Glu Gly His Tyr His Ala Asn Val Ala Tyr
                165                 170                 175
His Asn Ser Leu His Ala Ala Asp Val Ala Gln Ser Thr His Val Leu
                180                 185                 190
Leu Ala Thr Pro Ala Leu Glu Ala Val Phe Thr Asp Leu Glu Ile Leu
                195                 200                 205
Ala Ala Leu Phe Ala Ser Ala Ile His Asp Val Asp His Pro Gly Val
                210                 215                 220
Ser Asn Gln Phe Leu Ile Asn Thr Asn Ser Glu Leu Ala Leu Met Tyr
225                 230                 235                 240
Asn Asp Ala Ser Val Leu Glu Asn His His Leu Ala Val Gly Phe Lys
                245                 250                 255
Leu Leu Gln Ala Glu Asn Cys Asp Ile Phe Gln Asn Leu Ser Ala Lys
                260                 265                 270
Gln Arg Leu Ser Leu Arg Arg Met Val Ile Asp Met Val Leu Ala Thr
                275                 280                 285
Asp Met Ser Lys His Met Asn Leu Leu Ala Asp Leu Lys Thr Met Val
                290                 295                 300
Glu Thr Lys Lys Val Thr Ser Leu Gly Val Leu Leu Leu Asp Asn Tyr
305                 310                 315                 320
Ser Asp Arg Ile Gln Val Leu Gln Asn Leu Val His Cys Ala Asp Leu
                325                 330                 335
Ser Asn Pro Thr Lys Pro Leu Pro Leu Tyr Arg Gln Trp Thr Asp Arg
                340                 345                 350
Ile Met Ala Glu Phe Phe Gln Gln Gly Asp Arg Glu Arg Glu Ser Gly
                355                 360                 365
Leu Asp Ile Ser Pro Met Cys Asp Lys His Thr Ala Ser Val Glu Lys
                370                 375                 380
Ser Gln Val Gly Phe Ile Asp Tyr Ile Ala His Pro Leu Trp Glu Thr
385                 390                 395                 400
Trp Ala Asp Leu Val His Pro Asp Ala Gln Asp Leu Leu Asp Thr Leu
                405                 410                 415
Glu Asp Asn Arg Glu Trp Tyr Gln Ser Lys Ile Pro Arg Ser Pro Ser
                420                 425                 430
Asp Leu Thr Asn Pro Glu Arg Asp Gly Pro Asp Arg Phe Gln Phe Glu
                435                 440                 445
Leu Thr Leu Glu Glu Ala Glu Glu Asp Glu Glu Glu Glu Glu Glu Glu
                450                 455                 460
Gly Glu Glu Thr Ala Leu Ala Lys Glu Ala Leu Glu Leu Pro Asp Thr
465                 470                 475                 480
Glu Leu Leu Ser Pro Glu Ala Gly Pro Ala Pro Gly Asp Leu Pro Leu
                485                 490                 495
Asp Asn Gln Arg Thr
                500
```

HUMAN PHOSPHODIESTERASE TYPE IVC, AND ITS PRODUCTION AND USE

CROSS-REFERENCE TO RELATED APPLICATION

This application is a divisional of U.S. application Ser. No. 08/577,492, filed Dec. 22, 1995, now U.S. Pat. No. 5,851,78, issued Dec. 22, 1998.

This invention relates to human phosphodiesterase type IVC and its production, to conformers, analogues and fragments thereof, to nucleic acids encoding the enzyme, and to the use of the enzyme in drug screening and as an immunogen.

The role of cyclic AMP (CAMP) as a second messenger is well recognised. It is responsible for transducing the effects of a variety of extracellular signals, including hormones and neurotransmitters. The level of intracellular CAMP is regulated through both its synthesis by adenyl cyclases and degradation by cyclic nucleotide phosphodiesterases (PDE).

PDEs form a family of at least seven enzyme isotypes (I–VII) which differ in their affinity for cAMP and/or cGMP, subcellular localisation and regulation (Beavo J. A. and Reifsnyder D. H. (1990) Trends Pharmacol. Sci. 11 150–155; Conti M. et al. (1991) Endocrine Rev. 12 218–234). In the same way that receptors controlling the synthesis of CAMP have offered opportunities for developing selective therapeutic agents, the PDEs may afford similar possibilities for drug development. In fact the clinical effects of a number of drugs can be.rationalised on the basis of their selectivity for a particular POE isctype. For example, the cardiotonic drugs milrinone and zaprinast are PDE III and POE V inhibitors respectively. (Harrison S. A. et al. (1986) Mol. Pharmacol. 22 506–514; Gillespie P. G. and Beavo J. (1989) Mol. Pharmacol. 36 773–781). The anti-depressant drug, rolipram functions as a selective PDE IV inhibitor. (Schneider H. H. et aL (1986) Eur. J. Pharmacol. 127 105–115.).

The availability of POE isotype selective inhibitors has enabled the role of PDEs in a variety of cell types to be investigated. In particular it has been established that PDE IV controls the breakdown of CAMP in many inflammatory cells, for example basophils (Peachell P. T. et al. (1992) J. Immunol. 148 2603–2510 ) and eosinophils (Dent G. et al. (1991) Br. J. Pharmacol. 103 1339–1346) and that inhibition of this isotype is associated with the inhibition of cell activation. Consequently PDE IV inhibitors are currently being developed as potential anti-inflammatory drugs, particularly for the treatment of asthma in which the non-selective PDE inhibitor, theophylline, has been shown to have a therapeutic effect.

The application of molecular cloning to the study of PDEs has revealed that for each isotype there may be one or more isoforms. For PDE IV, it is has been shown that there are four isoforms (A, B, C and D) each coded for by a separate gene in both rodents (Swinnen J. V. et al. (1989) Proc. Natl. Acad. Sci. USA 86 5325–5329) and man (Bolger G. et al. (1993) Mol. Cell Biol. 13 6558–6571).

The existence of multiple PDE IVs raises the prospect of obtaining inhibitors that are selective for individual isoforms, thus increasing the specificity of action of such inhibitors. This assumes that the different PDE IV isoforms are functionally distinct. Indirect evidence in support of this comes from the selective distribution of these isoforms in different tissues (Swinnen et al. 1989; Bolger et al 1993; Obernolte R. et al. (1993) Gene 129 239–247, ibid) and the high degree of sequence conservation amongst isoforms of different species. To pursue the development of isoform selective inhibitors requires the availability of each enzyme type for evaluation.

To date full length cDNAs for human PDE IVA, B and D (Bolger et al. 1993 ibid; Obemolte et al. 1993 ibid; Mclaughlin M. et al. (1993) J. Biol. Chem. 268 6470–6476) and rat PDE IVA, B and D (Davis R. et al. (1989) Proc. Natl. Acad. Sci. USA 86 3604–3608; Swinnen J. V. et aL, (1991) J. Biol. Chem. 26 18370–18377), have been reported, enabling functional recombinant enzymes to be produced by expression of the cDNAs in an appropriate host cell. These cDNAs have been isolated by conventional hybridisation methods. However using this approach, only partial cDNAs for both human and rat PDE IVC have been obtained. (Bolger etal ibid. 1993 and Swinnen et al. ibid 1989 and International Patent Specification No. WO 91/16457.). These sequences are insufficient for producing a functional enzyme.

Although it might be expected that human PDE IVC cDNA could be fairly readily obtained by using conventional hybridisation approaches, this has not been the case, possibly due to the lower abundance of its mRNAs compared to the other three isoforms (Bolger et al. 1993 ibid). To overcome this problem we have devised a novel strategy for cloning the human PDE IVC mRNA (based on the approach -to primer design and described more particularly in the experimental section hereinafter) which has allowed us to obtain a functional enzyme by expression of the cDNA in mammalian, yeast and insect cells. This has enabled the properties of this enzyme to be compared to the A, B and D isoforms in terms of substrate kinetics and inhibition by PDE IV selective inhibitors.

Thus according to one aspect of the invention we provide an isolated nucleic acid molecule which encodes a human phosphodiesterase type IVC [PDE IVC].

Particular nucleic acids according to the invention comprise the nucleotide sequence depicted in FIG. 1 hereinafter, (SEQ ID No: 31) analogues and fragments thereof. The term "analogue" is meant to include all those DNA molecules which have the sequence shown in FIG. 1 but in which one or more nucleotides has been changed or one or more extra nucleotides is present. The term "fragment" is meant to include DNA molecules again having the sequence depicted in FIG. 1 but in which one or more nucleotides has been deleted. The term is also meant to include analogues in which one or more nucleotides has been deleted. It will be immediately understood that for an analogue or fragment to qualify as a DNA molecule according to the invention it must be able to encode a functional (catalytically active) PDE IVC. The DNA may comprise genomic DNA, cDNA or a combination of both.

The nucleic acids according to the invention may be obtained from any suitable human source using an appropriate probe as described herein. Once obtained, a nucleic acid may be modified by standard molecular biology and/or chemistry techniques, e.g. by use of oligonucleotide directed mutagenesis or oligonucleotide directed synthesis techniques, enzymatic cleavage or enzymatic filling in of gapped oligonucleotides, to obtain nucleic acid analogues or fragments of the invention. Alternatively, the nucleic acid may itself be used as a probe to obtain complementary copies of genomic DNA, cDNA or RNA from other human sources, using conventional genomic, cDNA and/or PCR cloning techniques.

The PDE IVC nucleic acid accor ding to the invention may be of use in therapy, for example where it is desired to modify the production of PDE IVC in vivo and the invention extends to such a use.

Knowledge of the nucleic acid according to the invention also provides the ability to regulate its activity in vivo by for example the use of antisense DNA or RNA. Thus, according to a further aspect of the invention we provide an antisense DNA or an antisense RNA of a gene coding for human phosphodiesterase type IVC, said gene containing nucleic acid comprising the nucleotide sequence of FIG. 1 herein, or an analogue or fragment thereof.

The antisense DNA or RNA can be produced using conventional means, by standard molecular biology techniques and/or by chemical synthesis. If desired, the antisense DNA and antisense RNA may be chemically modified so as to prevent degradation in vivo or to facilitate passage through a cell membrane, and/or a substance capable of inactivating mRNA, for example ribosyme, may be linked thereto, and the invention extends to such constructs.

The antisense DNA or RNA may be of use in the treatment of diseases or disorders in which the over- or unregulated production of PDE IVC has been implicated, for example in inflammatory diseases.

In particular, however, the nucleic acids according to the invention may be used to produce human PDE IVC or an analogue or fragment thereof. Thus, according to a further aspect of the invention we provide a recombinant human phospodiesterase type IVC or an analogue or fragment thereof.

The PDE IVC may in particular be an isolated enzyme, for example a partially purified cell-free enzyme, such as part of a cell supernatant or a purified enzyme substantially free of cellular or extraneous protein or other material. Analogues or fragments of the enzyme according to the invention are those proteins which still retain the human PDE IVC catalytic activity but which have one or more additional, fewer, or different amino acids to the naturally occurring enzyme.

A particularly useful protein according to the invention comprises the human PDE IVC amino acid sequence depicted in FIGS. 1 or 2 hereinafter (SEQ ID No: 32) and analogues and fragments thereof. A particular analogue is that comprising the amino acid sequence depicted in FIG. 1 together with the additional 5' amino acid sequence depicted in FIG. 7 hereinafter (SEQ ID No: 37).

Unexpectedly, we have found that is is possible to obtain the human PDE IVC enzyme of the invention in more than one catalytically active conformation, as demonstrated in the experimental section below, and the invention thus extends to all conformers of the isolated enzyme, analogues and fragments thereof. The ability of the PDE IVC sequence of the invention to direct the expression of different conformers of the enzyme which are distinguishable by their sensitivity to selective inhibitors in a catalytic assay was not predicted by the results for the expression of PDE IVA, B and D reported by others (e.g. Bolger et al, (1993) ibid. Livi et al, (1990) Mol. Cell Biol. 10, 2678–2686; Maclaughin et al (1992) ibid). The usefulness of such distinct conformers is that they enable the potency of novel inhibitors to be evaluated in the same assay format, namely inhibition of cAMP hydrolysis.

A particularly useful conformer according to the invention is that obtainable by expression of the PDE IVC enzyme in mammalian cells as described hereinafter. This form of the enzyme is characterised by its ability in an in vitro assay to distinguish between the R- and S-enantiomers of the known PDE IV inhibitor rolipram. Such a conformer, which maintains a stereo-selectivity for inhibition by R- and S-rolipram in vitro, and is distinct from other non-selective conformers, for example as obtainable by expression of the enzyme in yeast, is particularly advantageous for use to evaluate the properties of PDE IV inhibitors in an in vitro screen as described hereinafter.

As used herein the term "conformer" means any form of the PDE IVC enzyme as distinguished by its catalytic response to inhibitors, and extends for example to forms of the enzyme which may incorporate a post-translation modification, for example a phosphorylated form and other modified forms of the enzyme.

The PDE IVC protein, analogues or fragments thereof may be obtained by expression of the corresponding nucleic acids using appropriate expression vectors in any suitable procaryotic or eucaryotic host cell, using methods well known in the art (see for example "Current Protocols in Molecular Biology", Vol. I and II, Ansubel, F. M. et al (ed), Wiley Interscience, 1992), and the methods described in the experimental section hereinafter. Where desired the enzyme may be isolated from cell lysates and optionally purified using conventional techniques for example by ion-exchange and other chromatographic techniques.

Particular conformers may be obtained from different cell types. Thus the R- and S-rolipram stereoselective conformer according to the invention may be obtained for example by expression of the PDE IVC enzyme in mammalian cells, such as CHO or COS cells. Alternatively, a conformer of this type may be obtained by expression of the PDE IVC enzyme in insect cells, e.g. Sf9 cells. A non-selective conformer as described herein may be obtained from yeast cells.

The PDE IVC proteins according to the invention may be used to screen for agents which modulate the action of the protein, for example phosphodiesterase inhibitors, especially PDE IVC isoform selective inhibitors, for use in medicine, and the invention is to be understood to extend to such a use, and to screens containing the PDE IVC protein of the invention.

Thus according to a further aspect of the invention we provide a method for selecting a compound which modulates the action of human phosphodiesterase type IVC which comprises contacting a test compound with a recombinant human phosphodiesterase type IVC in a test system containing a substrate for the enzyme and monitoring any modulation of the action of the enzyme due to the presence of the test compound.

In this aspect of the invention the recombinant PDE IVC enzyme may be an isolated enzyme, in particular a R- and S-rolipram stereoselective conformer as described herein. Alternatively, the enzyme may be expressed during the operation of the assay from a cell, particularly a mammalian or insect cell, transformed with the PDE IVC nucleic acid according to the invention. Test compounds for use in this aspect of the invention may be synthetic or naturally occurring.

Such a screen may be especially useful for selecting a PDE IVC isoform selective inhibitor for use in medicine, and the invention extends to inhibitors selected in this way. Use of the R- and S-rolipram stereo-selective conformer of the invention as the target enzyme in the screen can be expected to provide for the selection of inhibitors with advantageous properties since based on the results described hereinafter, this form of the enzyme may be assumed to more closely model the native enzyme than non-selective conformers, for example those produced in a host such as yeast. Inhibitors selected in this way may be of use in the prophylaxis and treatment of inflammatory diseases, for example in the prophylaxis and treatment of asthma, especially inflamed lung associated with asthma. The inhibitors may be formulated for use as pharmaceutical compositions, together with one or more pharmaceutically acceptable carriers, excipients or diluents in accordance with conventional practice.

Antibodies may also be generated to one or more epitopes of the proteins according to the invention using conventional immunization and recombinant DNA techniques and the invention extends to the use of a human PDE IVC according to the invention as an immunogen.

Thus, for example polyclonal antibodies may be obtained from the sera of animals immunised with a phosphodiesterase according to the invention or an analogue or fragment thereof. Any suitable host, for example BALB/c mice where it is desired to obtain a mouse polyclonal antibody, may be injected with the immunogen, the serum collected and the antibody recovered therefrom. Monoclonal antibodies may be obtained from hybridomas derived from the spleen cells of an animal immunised as just discussed and fused to an appropriate "immortal" B-tumour cell. In each instance, the antibody may be recovered from either the serum or the hybridoma by making use of standard purification and or concentration techniques, for example by chromatography, using for example Protein A or by other affinity chromatography employing a phosphodiesterase of the invention or an analogue or fragment thereof Once a cell line, for example a hybridoma, expressing an antibody has been obtained it is possible to clone therefrom the cDNA and to identify the variable region genes encoding the desired antibody, including the sequences encoding the CDRs. From here, other engineered antibodies may be obtained by preparing one or more replicable expression vectors containing at least the DNA sequence encoding the variable domain of the antibody heavy or light chain and optionally other DNA sequences encoding remaining portions of the heavy and/or light chains as desired, and transforming an appropriate cell line, e.g. a non-producing myeloma cell line, such as a mouse NSO line, in which production of the antibody will occur. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al [Molecular Cloning, Cold Spring Harbor Laboratory, New York, 1989]; DNA sequencing can be performed as described in Sanger et al [PNAS 74, 5463, (1977)] and the Amersham International pic sequencing handbook; and site directed mutagenesis can be carried out according to the method of Kramer et al [Nucl. Acids Res. 12, 9441, (1984)] and the Anglian Biotechnology Ltd handbook. Additionally, there are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews [ed. Tombs, M P, 10, Chapter 1, 1992, Intercept, Andover, UK] and in International Patent Specification No. WO 91109967.

Polyclonal, monoclonal and engineered antibodies obtained in the above general ways and which are capable of binding recombinant human PDE IVC, especially a R- and 5-rolipram stereoselective conformer thereof form a further feature of the invention. Such antibodies may be of use, for example, in analytical tests, PDE IVC purification procedures and the like.

The invention is now described in the Examples below, with reference to the following Figures.

SUMMARY OF FIGURES

FIG. 1: DNA (SEQ ID NO: 31) and amino acid sequence (SEQ ID NO: 32) of human PDE IVC.

FIG. 2: Alignment of human PDE IV amino acid sequences. Gene A (SEQ ID NO: 33); Gene B2 (SEQ ID NO: 34); Gene C (SEQ ID NO: 32); and Gene D (SEQ ID NO: 35).

FIG. 3: Alignment of human (SEQ ID NO: 32) and rat (SEQ ID NO: 36) PDE IV amino acid sequences.

FIG. 7: DNA sequence (SEQ ID NO: 36) and amino acid sequence (SEQ ID NO: 37) of alternative 5' end of human PDE IVC.

EXPERIMENTAL PROCEDURES

Figure 4:
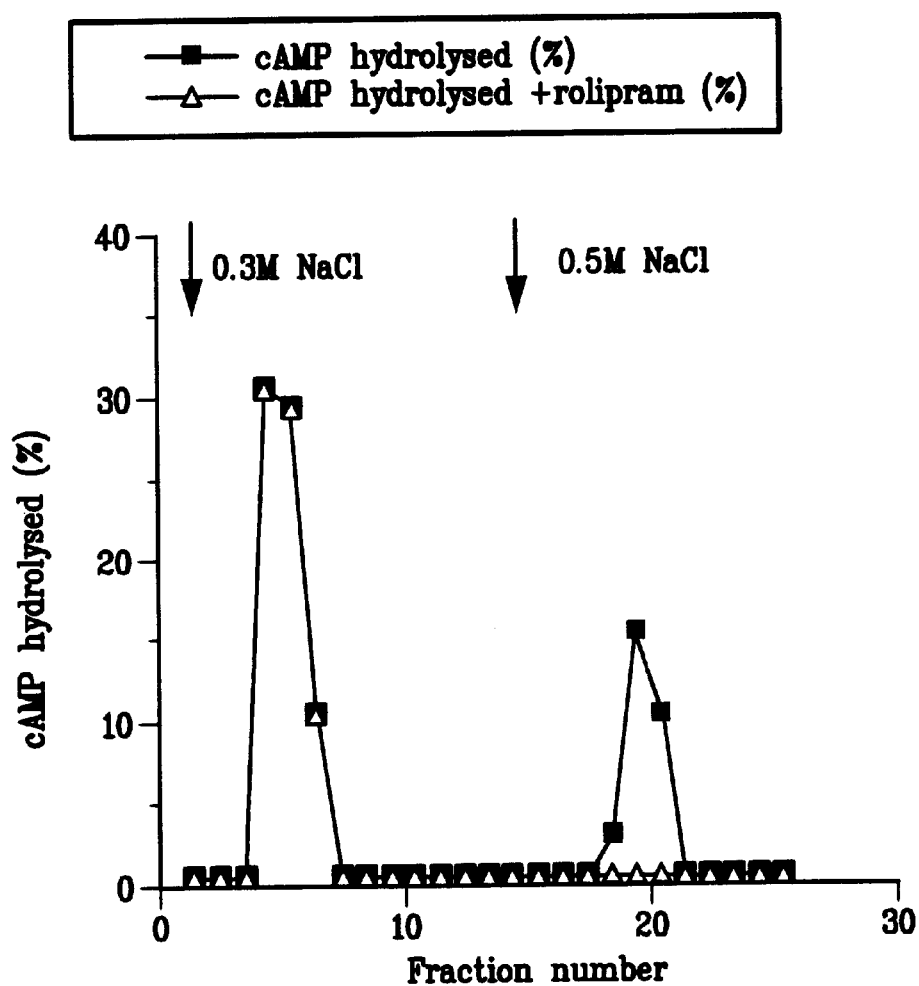
FIG. 4: Separation of recombinant PDE IVC from yeast PDE activity by monoQ Sepharose ion-exchange chromatography.

RT.PCR Analysis.

To identify a source of gene C mRNA, a number of cell lines were assayed for isoform mRNAs by reverse transcription coupled to polymerase chain reaction (RT.PCR). Total RNA was prepared using RNAzol (Biogenesis) and polyA+ mRNA selected by affinity chromatography using oligodT cellulose. 50 ng of first strand cDNA prepared by reverse transcriptase was amplified with the following pairs of gene specific primers for 40 cycles using the conditions, 94° C. 1 min, 55° C. 1 min, 72° C. 3 min.

Gene A
Forward primer R39. SEQ ID No: 1
5' GATC GGATCCGCGGCTGCCATCCACGATGTGGATCAC CCTGGGG 3'
Reverse primer R4148. SEQ ID No: 2
5' TTTTTGGATCCGGGATCAGGTAGGGTCTC 3'
Gene B
Forward primer R4138. SEQ ID No: 3
5' TTTTTAAGCTTCAGCTCATGACCCAGATMG 3'
Reverse primer R4143. SEQ ID No: 4
5' TTTTGGATCCGATAGMATGTTCATCTCCAC 3'
Gene C
Forward primer R5130. SEQ ID No: 5
5' TTTTTGAATTCGATATCTTCCAGMCCTCAGCGC 3'
Reverse primer R5192. SEQ ID No: 6
5' TTTTTGAATTCCTMGTCCTCTGGTTGTCGAG 3'
Gene D
Forward primer R5205. SEQ ID No: 7
5' TTTTTGAATTCAGAGTTGTCTGGTMCCGGC 3'
Reverse primer R5206. SEQ ID No: 8
5' TTTTGAATTCGTTACGTGTCAGGAGACG 3'
NB restriction sites in the primers are underlined.
Isolation of gene C cDNA.

A partial PDE IVC CDNA clone was isolated from U87 cell mRNA using RT.PCR. A 5' PCR primer was designed based on the prediction that a short stretch of amino acid sequence towards the amino terminus of gene C would be identical to that of the A,B,D isoforms previously cloned. A mixture of oligonucleotides were synthesised that would be expected to hybridise to the DNA sequence encoding this segment of the gene. Two features of the primer design advantageously minimise the number of different sequences required. Firstly, codon usage was based on the sequence of the other three PDEIV isoforms. Secondly, only the last five codons were varied. An ATG was added to the 5' end of the PDE sequence to enable any amplified sequences to be directly expressed. A Hind3 restriction enzyme cloning site was also incorporated into the primers. The target amino acid sequence and oligonucleotides are shown below.

```
                M  E  T  L  E  E  L  D  W  C
5' CGCGCGAAGCTTATGGAGACGCTGCAGGAGCTAGACTGGTGT 3'
                                        AT G
```

The 3' PCR primer was R5192 shown above and incorporated an EcoR1 site for cloning. Amplification was carried out using the conditions described above. A 1500 bp PCR product was obtained and sub-cloned into the commercially available vector pSP73 to produce the plasmid pDEU1. 12 independent clones were sequenced on both strands and identified as gene C by reference to the published partial sequence.

To isolate the 5' terminus of PDE IVC and the initiating methionine residue the protocol of a commercial PCR based strategy (5' Amplifinder™ Race, Clontech) was followed. The RACE method rapid amplification of cDNA ends) was first described by Frohman et. al. [1988] Proc. Natl. Acad. Sci. USA 85 8998–9002] and Belyauskey et al. [(1989) Nucl.Acids Res. 17 2919–2932]. The Clontech method is a modified version of that described by Edwards et al [(1991) Nucl. Acids Res. 19 5227–5232], involving single-stranded ligation of a nucleotide anchor to the 3' end of the first-strand cDNA, thus avoiding homopolymeric tailing. —

As with the partial PDE IVC clone (PDEU1) described above, first strand cDNA was synthesised from 2 ug of U87 cell mRNA using R6333 as the priming oligonucleotide.
R6331. SEQ ID No: 10
5'-TTTCTCGAGGGTrICGGACAGGTGGGTCMCTC CCG-3'
R6332. SEO ID No: 11
5'-T1 CTCGAGGCCACTGATCCGGGACATGGGCTG-3'
R6333, SEO ID No: 12
5'-TTTCTCGAGCCACTTGTTGGTGTCTTCTAGCTC-3'

The primary PCR reaction consisted of 5 ul of single-stranded ligation mix, 5 U Taq polymerase, 2 ul dimethyl-sulphoxide (DMSO), 250 uM deoxyribonucleotide triphosphates (dNTPs), 0.2 uM anchor primer, 0.2 uM oligonucleotide R6332 and H$_2$O to a total volume of 50 ul. The reaction was amplified for 35 cycles under the following parameters, 95° C./1 min, 65° C./1 min, 72° C./1 min. The secondary PCR reaction consisted of, 2 ul of a 1:10 dilution of the primary PCR mixture, 5 U Taq polymerase 2 ul DMSO, 250 uM dNTPS, 0.2 uM anchor primer, 0.2 uM oligonucleotide R6331 and H$_2$O to a total volume of 50 ul. Amplification was carried under the same parameters as in the primary PCR reaction.

The products of the secondary PCR reaction were digested with the restriction enzymes EcoR1 and BamH1, the sites which are contained within the ligated anchor and within the PDE IVC sequence respectively. The fragments were cloned into EcoR1/BamH1 digested psP65 vector (Promega), recombinant colonies were identified by PCR screening, sequenced on both strands and confirmed as PDE IVC. The resulting plasmid containing a 470 bp fragment was named pDER2. Translation of the nucleotide sequence identified a methionine residue at position 336 bp unfortunately, the reading frame remained open and it could not be confirmed as the initiating methionine. The clone did however contain all of the Upstream Conserved Region 1 (UCR 1) recently described (Bolger et al. ibid 1993).

The RACE method was repeated again this time using oligonucleotides derived from the new 5' sequence described above.

The primary and secondary PCR reactions were carried out under the same conditions as described above using oligonucleotides R6532 and R6533 respectively
R16532. SEQ ID No. 13
5'-TTTGGATCCGGCCAGGACCTGGGCMAGGGCG-3'
R6533. SEQ ID No: 14
5'-TTTGGTCGGCCTTGGGCGAGAGTTCATAGTCGC-3'

The products of the secondary PCR reaction were restricted with EcoR1 (anchor site) and BamH1 (also contained within the gene specific oligo R6533) and cloned into commercially available pSP65. Recombinant colonies were identified by PCR analysis and plasmid DNA was isolated and sequenced on both strands. Sequence analysis revealed that all four clones were identical, however, two of the four clones had extended 5' sequence. When translated all of the clones contained a 5' termination codon in the same position. The first initiating methionine residue downstream corresponded to the methionine residue described in PDER.2.

To construct a catalytically active full length PDE IVC gene, the internal BamH1 site was used to add the new 5' sequence to the partial clone. pDEU1 and pDER2 were digested with BamH1 and EcoR1 to release two fragments of 1424 & 470 bp respectively. The eukaryotic expression vector pEE7hcmv (Stephens P. and Cockett M. [(1989) Nucl.Acids Res. 17 7110] was digested with EcoR1. A three-way ligation was carried out and transformants were screened by PCR to determine the orientation of the inserts. Plasmid DNA was purified and sequenced on both strands. The plasmid was named pDEU7. The Hind 3-EcoR1 fragment containing the full length gene C from pDEU7 was inserted into the yeast expression vector pYES (InVftrogen) to produce the vector pDEU8.

Isolation of cDNA Clones for Gene A

A partial cDNA for gene A was isolated by PCR from a cDNA library prepared from PMA stimulated U937 cells using published sequence information (Livi G. et al. (1990) ibid)). Subsequently a conserved region probe form this cDNA was used to isolate a full length cDNA clone from a human frontal cortex cDNA library by hybridisation and washing at moderate stringency (final wash 2×SSC, 0.5% SDS at 60° C.). The sequence of this clone is identical to that of Bolger et al. ibid (1993) with following minor differences G>A at 724 bp=met to ile change, G>A at 1238 bp silent change.

The full length gene for PDE IVA was introduced into pEE7 and pYES vectors for expression in COS and yeast cells respectively.

Northern Blot Analysis

The distribution of PDE IV isoform mRNAs in different human tissues was analysed by northern blotting. Human multiple tissue northern blots purchased from Clontech were hybridised with isoform specific probes generated by PCR from the 3' non-translated region of each gene. Either HL-60 genomic DNA (probes A and C) or a cDNA library prepared from eosinophil enriched mRNA (probes B and D) were used as templates for PCR amplification with the following pairs of primers and the conditions described above.

Gene A.
Forward primer R6069. SEQ ID No:15
5' TTTTTAACTTGACCTCTGTCCCTGTTCCCCTCC 3'
Reverse primer R6095. SEQ ID No: 16
5' TTTTTGGATCGGCTGGAAGACTGAGCCTGGACC 3'
Gene B.
Forward primer R607. SEQ ID No: 17
5' TTTTTCGCATGCCAGCTATGTGGTAGGG 3'
Reverse primer R6072. SEQ ID No. 18
5' TTTTTGAATTGGCAGACAAGGGACAGTGAGAAG 3'
Gene C.
Forward primer R6039. SEQ ID No: 19
5' TTTTTAAGCTTCAGCCCTGCGTGAACTGCAGG 3'
Reverse primer R6040. SEQ ID No: 20
5' TTTTTGAATTCGACTCAAGAGTGACCACTGGAG 3'
Gene D.
Forward primer R6073. SEQ ID No: 21
5'TTTTTTMGCTTCCAAAGTGCATGTCACATGCCAC 3'
Reverse primer R6074. SEQ ID No. 22
5' TTTTTGMTTCGAGGTCAGTGCAGCTCACTGAAC 3'

Gene-specific probes were radiolabelled with $^{32}$P.dCTP using random priming. RNA blots were hybridised for 1 h at 65° C. in Expresshyb™ (Clontech) and washed for 40 min at room temp. in 2×SSC, 0.05% SDS and then for 40 min at 65° C. in 0.1×SSC, 0.1% SDS. Blots were exposed to X-ray film with intensifying screens at −70° C. for up to 7 days.

Construction of PDE IVA and PDE IVC Deletion Mutants.

Deletion analyses of rat PDE IVD (Jin C. (1992) J.Biol.Chem. 27 18929–18939) and PDE IVB (Pillai R. et al. (1993) Proc.Natl.Acad.Sci.USA 90 11970–11974) have defined the minimum enzyme sequence required for catalytic activity. Corresponding deletions were made to both human PDE IV A and C enzymes and the activity of the resulting enzymes evaluated following transient expression in COS cells.

PDE IVA PCR was used to construct a plasmid (pDEFC18) containing the first 129 bp (Met1 to Ile 43) of the PDE IVA gene. In addition a 3' BamH1 restriction enzyme site was introduced into the sequence. The PCR primers were as follows:
R 5836 forward primer. SEQ ID No: 23
5'TTTTAAGCTTCCACCATGGMCCCCCGACCGTC 3'
R 5840. reverse primer. SEQ ID No: 24
5' TTTTGCGCTGCGGATCCGGATGGG 3'

A mutant deleted to the beginning of the catalytic domain (Ile43-Gln 330; Bolger et al. 1993 ibid) was produced by PCR using the following primers:
R 5839. forward primer. SEQ ID No: 25
5' TTTTTGGATCCATGTCCCAAATCAC 3'
R 5882. reverse primer. SEQ ID No: 26
5' TTTTTGAATTCCTCGAGCACCGACTCATCG 3'

The PCR fragment was restricted with BamH1 and EcoR1 and cloned into the plasmid, pDEFC18 described above to produce the vector pDEFC23. Following sequencing this vector was restricted with Hind3 and Xho1 and inserted into Hind3/Xbal restricted pEE7 together with a Xho1/Xba1 fragment corresponding to the remaining 3' portion of gene A. The final plasmid was designated pDEFC24.

PDE IVC The mutant enzyme deleted to the position in PDEIVC corresponding to the PDE IVA deletion (Metl80) was produced by PCR using the following primers:
26272. forward primer. SEQ ID No: 27

5' GCGCGC AAGCTTGCCACCATGTCCCGGATCAGTGGCCTAC 3'
26273. reverse primer. SEQ ID No. 28
5' GAACACAGCCTCGAGGGCGGGCGTAGCC 3'

The PCR amplified fragment was restricted with Hind3 and Xho1 and inserted into psp73 to produce the plasmid pDEU9. Following sequencing of the insert this plasmid was then restricted with Hind3 and Xhol and ligated to a Xho1/EcoR1 fragment from pDEU7 containing the remaining 3' portion of gene C and inserted into Hind3/EcoR1 restricted pEE7. The resulting plasmid was designated pDEU10.

Expression Sytsems

Recombinant PDE IV enzymes were produced in COS cells by transient expression as described by Whittle N. et al. [(1987) Prot. Engineering 1 499–505]. Briefly 5×10 cells/ml were transfected with 10 ug of plasmid. After 3 days in culture cells were washed with PBS and lysed by brief sonciation in 50 mM TES buffer, pH 7.6, (N. tris [hydroxymethyl]methyl) 2-aminoethane sulphonic acid containing proteases inhibitors (50 uM leupeptin, 1 uM pepstatin, 1 um phenylmethylsulphonylfluoride, 2 uM benzamidine). The cell homogenate was centrifuged ×12000 g for 10 min. and assayed for PDE IV activity.

For expression of full length PDE IVA and C cDNAs in Chinese hamster ovary cells (CHO) L761 cells, the plasmids, pDEFC17 and pDEU7 were introduced into the cells by calcium phosphate precipitation (Cockett M. et al. (1991) Nucl. Acids Res 19 319–325).

For expression of PDE IVA and C in yeast cells, the two genes were inserted into the vector pYES (InVitrogen) as either Hind3/Xba1 (gene A) or EcoR1 (gene C) fragments isolated from pDEFC17 and pDEU7 vectors respectively. The resulting plasmids were designated as pDEFC 32 and pDEU8 respectively. Yeast cells (B7542: alpha, ura-3,trp1+, Leu2delta, pep4: His3, prBdelta 1.6R can 1, gal) were transformed with pDEFC32 and pDEU8 vectors using the lithium acetate method (Ito H. et al. (1983) J.Bacteriol. 51 163–168). Ura3 positive prototrophs were isolated and grown at 30° C. to an $OD_{600}$=1.0 in minimal media containing 2% glucose and 50 mg/ml leucine. Cells were recovered by centrifugation, washed and resuspended at $OD_{600}$=0.5 in minimal media containing 2% galactose to induce PDE IV expression. At an $OD_{600}$=1.0 cells were harvested, washed and broken in TES buffer plus proteases (see above) by milling with glass beads (425–600 um) at 4° C. The homogenate was clarified by centrifugation at 100,000 g for 30 mins at 4° C. For large scale production of PDE IV enzymes, yeast cells were grown to 1.8 L scale in a fed-batch fermenter PDE expression was routinely induced by addition of galactose at $OD_{600}$=30–40 and cells harvested approximately 48 hours later.

For expression of PDE IVC in insect cells, the gene was inserted into the transfer vector, pVL 1392 (In Vitrogen), as an EcoR1 fragment isolated from pDEU7. The resulting plasmid was designated as pDEU16. Sf9 cells were cotransfected with purified AcNPV linear DNA (Pharmingen) and pDEU16 transfer vector as described by Summers and Smith (1987) Texas Agricultural Experimental Station Bulletin No. 1555. Growth, plaque purification and titration of viruses were carried using standard procedures. For production of protein, cells were grown in spinner flasks to 2×10$^6$/ml, infected with a multiplicity of infection of 10 and harvested after 60 h.

Enzyme Assays

Enzyme reactions were carried out at pH 7.6 in 50 mM TES buffer containing 10 mM $MgCl_2$, 3',5' cAMP (0.1 uM ³H-labelled 0.74–1.1 TBq/mmol) 5'AMP (2.5 uM ¹⁴C, 1.85–2.2 GBq/mmol) for 30 min at 30° C. Sufficient enzyme preparation was added to hydrolyse not more than 20% of substrate under these conditions. For Km determinations, unlabelled cAMP was added to achieve substrate concentrations in the range 0.1–20 uM. Reactions were stopped by rapid inactivation of enzyme by addition of trifluoroacetic acid to a final concentration of 1%. Substrate and product of reaction were separated as described by Smith et al. [(1993) Analyt. Biochem. 214 355–357] and the [³H] 5'AMP product analysed by scintillation counting. Correction for losses of [³H] 5CAMP during separation was made by reference to [¹⁴C] 5'AMP included in the reaction mixture.

Isolation of Human Beta 2 Adrenergic Receptor Gene.

The human beta 2 adrenergic receptor gene (Kobilka B. et al. (1987) J.Biol. Chem. 262 7321–7327) was isolated from HL-60 cells genomic DNA by PCR using the following primers:

R5690, forward primer. SEQ ID No: 29
5' GCGCGC<u>AAGCTT</u>CGCTTACCTGCCAGACTGCGC 3'
R 5691. reverse primer. SEQ ID No: 30
5' GCGCGCG<u>AATTCT</u>TCTGTTTAGTGTTCTGTTGGG 3'

The PCR fragment was restricted with Hind3 and EcoR1 and inserted into pEE6 BgI2 neo vector (Stephens P. and Cockett M. (1989) Nucl. Acids Res. 17 7110) for expression in mammalian cells. The plasmid was named pRO1 44.

Measurement of Intracellular cAMP in Isogroterenol Stimulated CHO Cells Co-tranfected with Beta 2 Adreneraic Receptor and PDE IV A or C.

Transfected cells were harvested with non-enzymatic cell dissociation reagent (Sigma) washed three times and re-suspended in Dulbecco's phosphate buffered saline containing 0.1% BSA and 0.1% glucose (DPBS+). The cells were incubated with 10 uM inhibitor (or solvent control, 0.1% DMSO) in DPBS+for 10 min at 37° C. The cell suspension was stimulated with isoproterenol (0.001–1 uM) for 2 min. The cells were pelleted at 12000 g and resuspended in 400 uL of boiling assay buffer 1s (DuPont cAMP measurement kit). The samples were heated in a boiling water bath for 10 min and frozen before being assayed for cAMP using a commercial cAMP radioimmunoassay (DuPont).

SDS-PAGE and Western Blotting.

SDS-PAGE was carried out according to Laemmli (1970) Nature 227 680–685 using 10% (w/v) acrylamide gels. For Western blotting proteins were transferred to nitrocellulose and probed with a rabbit polyclonal antiserum raised to a C-terminal PDE IVC peptide.

Results

Cloning and Sequence Analysis of Human PDE IVC.

A series of PCR amplification steps was used to assemble a putative full length version of the human PDE IVC mRNA The composite sequence of the three overlapping cDNAs that were isolated is shown in FIG. 1, SEQ ID No: 31. The sequence contains an ORF of 1818 bp in length which predicts a 605 amino acid protein with a calculated molecular mass of approximately 66.5 kD. Evidence was also obtained for a second PDE IVC mRNA which diverges from the first sequence at position 259 bp (FIG. 1) This represents a point of alternative exon splicing in both human PDE IVA and D (Bolger et al. ibid 1993). It is predicted therefore that the primary transcript of human PDE IVC gene in common with other PDE IV genes is differentially processed to produce at least two mRNAs that differ in their 5' sequence.

FIG. 2 shows an alignment of the human PDE IVC primary amino acid sequence (SEQ ID No: 32) with sequences of the three other cloned human PDE IVs, GENE A (SEQ ID No: 33), GENE B2 (SEQ ID No: 34) and GENE D (SEQ ID No: 35). The PDE IVC is highly homologous to the PDE IVA, B and D sequences particularly in the two upstream conserved regions (UCR1 and UCR2, as defined by Bolger et al. (1993), ibid) and central catalytic region, where amino acid identity is >/=90%. Outside these homologous domains, the sequence in common with the other PDE IVs is isoform specific particularly C terminal of the catalytic domain. Comparison of the human PDE IVC with the partial rat PDE IVC sequence shows that these isoform-specific regions have been relatively conserved between isoforms of different species. Thus overall the sequence of human PDE IVC is probably more homolgous to the same isoform in different species than different isoforms of the same species (FIG. 3), SEQ ID No: 36. This apparent conservation of PDE IV isoforms implies conservation of functional significance.

The sequence of the alternative 5' end for human PDE IVC is shown in FIG. 7, SEQ ID No: 31. This sequence contains an ATG at position 63 bp which may represent the start site of this mRNA. However, since the reading frame remains open upstream of this ATG, this cannot be conclusively assigned as the initiation site.

Expression in COS Cells and Evaluation of Catalytic Activity.

Recombinant human PDE IVC was produced by transient expression in COS cells. The product was recovered in the soluble fraction of the lysed cells (×12000 g supernatant) and migrated with an apparent molecular weight of approximately 80 kD on SDS PAGE as revealed by Western blotting using a human PDE IVC specific polyclonal rabbit antiserum. The PDE IV activity expressed in COS cells was markedly inhibited by the PDE IV selective inhibitors, rolipram and denbufylline and also by the broad spectrum PDE inhibitor IBMX (Table 1). This inhibition profile of PDE IVC was compared to that of PDE IVA also produced by transient expression in COS cells. Most interestingly, the PDE IVC enzyme showed significantly greater sensitivity to both rolipram and denbufylline compared to PDE IVA (Table 1). In additon the PDE IVC enzyme demonstrated stereoselectivity for the R-form of rolipram, whereas the PDE IVA did not. It has been reported that the IC$_{50}$'s for rolipram inhibition of PDE IVs A, B and D are very similar at around 200–500 nM (Livi et al. (1990); Maciaughlin et al. (1993); Bolger et al. (1993) ibid.) Thus the PDE IVC enzyme obtained from COS cells appears to exhibit distinct pharmacological properties from the other PDE IV isoforms, which can be exploited in the development of isoform selective inhibitors.

TABLE 1

| | (IC50 nM) | |
|---|---|---|
| Enzyme | PDE IVA | PDE IVC |
| Inhibitor | | |
| Rolipram (racemate) | 205 | 32 |
| R-rolipram | 292 | 21 |
| S-rolipram | 145 | 317 |
| Denbufylline | 2295 | 61 |
| IBMX | 10549 | 2164 | mRNA Tissue and Cell Distribution.

The distribution of the PDE IVC mRNA(s) was investigated by both Northern blotting and reverse-transcription coupled to PCR (RT.PCR).

The results are summarised in Tables 2 and 3. The Northern blotting data indicate that PDE IV isoform mRNAs are widely distributed in human tissues with isoform C mRNA least abundant. Each isoform produces at least two mRNA species of distinct size (A=4.5kb, B=4 &5 kb, C=6.0 kb, D=7.5–8.0 kb). Brain and skeletal muscle appear to have the highest levels of all isoform mRNAs.

The results of RT.PCR using the human gene primers to detect isoform mRNAs in both human tissue culture cells and rat tissues confirms that PDE IV mRNAs are widely distributed though the apparent levels of each isoform mRNA varies. Gene C mRNA appears to be more abundant than A,B, or D in cells derived from dorsal root ganglia and testes in rat. This latter result is consistent with data reported previously by Swinnen et al. (1989) ibid. Interestingly, treatment of cell lines with $bt_2$ cAMP leads to an increase in some but not all PDE IV isoform mRNAs. Thus in the human cells HL-60 and SKN.SH, levels of C and D but not A and B are elevated.

TABLE 2

| TISSUE | A | B | C | D |
|---|---|---|---|---|
| Heart | ++ | ++ | ND | + |
| Brain | +++ | ++++ | ++ | ++++ |
| Placenta | + | + | ND | + |
| Lung | ++ | ++ | ND | ++++ |
| Liver | + | + | ND | + |
| Skeletal Muscle | ++++ | ++++ | +++ | +++++ |
| Kidney | ++ | ++ | ND | ++++ |
| Pancreas | ++ | ND | ND | (+/−) |
| Spleen | + | ++ | ND | + |
| Thymus | + | + | ND | ++ |
| Prostate | + | ++ | ND | +++ |
| Testes | ++ | + | ND | (+/−) |
| Ovary | + | + | + | + |
| Small Intestine | + | + | + | ++ |
| Colon | + | + | ND | ++ |
| PBL | ++ | +++ | ND | ++++ |

ND = Not Detected

TABLE 3

| | A | B | C | D |
|---|---|---|---|---|
| CELLS | | | | |
| U937 | − | + | +/− | + |
| Jurkat | + | − | − | + |
| T98G | + | + | +/− | + |
| U87 | + | + | + | + |
| SKNSH | + | + | + | + |
| HL60 | + | + | −/+ | + |
| Neutrophils | − | + | + | + |
| B50 (rat) | + | + | − | not determined |
| NG115 (rat) | + | + | − | not determined |
| TISSUES (rat)* | | | | |
| Liver | + | − | + | + |
| Testes | + | + | ++ | + |
| Brain | + | + | +/− | + |
| Heart | − | − | − | − |
| Kidney | − | − | − | − |
| DRG | + | + | + | − |
| $Bt_2$ CAMP stimulated CELLS | | | | |
| HL60 0h | + | + | −/+ | + |
| HL60 2h | + | + | + | ++ |
| HL60 6h | + | + | + | ++ |
| SKNSH 0h | − | − | − | ++ |
| SKNSH 2h | − | − | + | ++ |
| SKNSH 6h | − | − | + | not determined |

*Rat tissue PCR carried out using human primers.

Expression in Yeast and CHO Cells.

Both PDE IVC and PDE IVA were expressed in yeast and CHO cells; The CHO cell lysates were analysed for PDE activity and inhibition by rolipram. $IC_{50}$'s of 43 and 287 nM for C and A respectively were obtained which are consistent with results for the enzymes produced in COS cells (Table 1).

Yeast express two endogenous PDE activities (Londesborough J. and Souranta K. (1983) J. Biol. Chem. 258 2966–2972; Souranta K. and Londesborough J. (1984) J.Biol.Chem. 259 6964–6971). Therefore, yeast cell lysates were fractionated by ion-exchange chromatography to separate the recombinant PDE IV activity from the host cell enzymes (FIG. 4). The sensitivity of the fraction enriched for PDE IVC activity to inhibition by rolipram was evaluated. Unexpectedly, this enzyme demonstrated limited enantiomeric selectivity for the R and S forms of rolipram and generally much higher $IC_{50}$ values (Table 4). Thus the PDE IVC enzyme produced in yeast appears distinct from that produced in mammalian cells (COS, CHO). By contrast, PDE IVA produced in yeast showed similar rolipram inhibition to the enzyme expressed in COS and CHO cells (Tables 1 and 4). These results could be explained in terms of a specific post-translational modification of the PDEIVC enzyme that only occurs in mammalian cells, for example phosphorylation. It follows that such a modification does not occur to PDE IVA or at least if It does, it has no effect on the ability of the enzyme to be inhibited by rolipram.

In either event knowledge of the primary sequence of PDE IVC is necessary to investigate this phenomenon.

TABLE 4

| | $IC_{50}$(nM) | | | |
|---|---|---|---|---|
| | Yeast | | CHO | |
| Inhibitor | A | C | A | C |
| R-rolipram | 298 | 1648 | 251 | 186 |
| S-rolipram | 619 | 4771 | 1004 | 1428 |
| Rolipram (racemate) | not determined | 1638 | 287 | 43 |

Expression of PDE IVC in Insect Cells.

The PDE IVC cDNA was expressed in insect cells using the baculovirus system. Sf9 cell lysates were assayed for PDE activity and inhibition by the enantiomers of rolipram. $IC_{50}$ values were obtained for R-rolipram (104 nM) and for S-rolipram (600 nM). Thus the potency of R-rolipram on this version of the enzyme is closer to that of the COS enzyme than the yeast produced PDE IVC.

Comparison of PDE IVC Expressed in Yeast, COS and Sf9 Cells.

The kinetics of cAMP hydrolysis for the different preparations of PDE IVC produced in yeast, COS and Sf9 cells were compared (Table 5). All enzyme preparations demon strated simple Michaelis-Menten kinetics with $K_m$ values in the low uM range (Table 5). $V_{max}$ values of 0.3 and 0.6 μmoles/min/mg were estimated for the partially purified enzymes from yeast and Sf9 cells.

TABLE 5

| Enzyme source | Km (μM) | $V_{max}$ (μmoles/min/mg) |
|---|---|---|
| Yeast | 2.5 | 0.6 |
| COS | 0.3 | — |
| Sf9 | 1.1 | 0.3 |

These data are consistent with reports in the literature for preparations of purified PDE IV enzymes e.g. Wilson et al (1994) Biochem. J. 304. 407; Conti M et al (1995) Biochemistry 3, 7979.

The principal difference between the preparations of the PDE IVC enzyme is in their response to selective PDE IV inhibitors exemplified by rolipram (see Tables 3 and 4). To show that these differences were not due to a contaminant in either one of the preparations, a mixing experiment was carried out. Thus equal amounts of PDE IVC enzyme activity produced in yeast and COS cells were mixed and the inhibition of the mixture by rolipram compared to each component assayed separately. The results (Table 6 and FIG. 5) confirm that the PDE IVC enzymes from yeast and COS cells are distinct, since a 1:1 mixture of the two produces an intermediate value for rolipram inhibition.

TABLE 6

| Enzyme Source | $IC_{50}$ (nM) |
|---|---|
| COS | 75 |
| Yeast | 2051 |
| COS/yeast (1:1 mixture) | 596 |

Deletion of PDE WC

Evidence for the biochemical uniqueness of PDE IVC was obtained by comparing the effect of deleting the enzyme to the minimum sequence required for catalysis identified for PDEIV A, B and D. Equivalent deletion mutants of PDE IV C and A were prepared and expressed in COS cells. The results, (Table 7) showed that while both deleted enzymes were expressed only PDEIVA was catalytically active. This indicates that in PDE IVC unlike the other three PDE IV isoforms, catalytic activity requires sequences further towards the amino terminus of the protein

TABLE 7

| Construct (pmol/min/ul) | Expression (Wblot) | Catalytic activity |
|---|---|---|
| PDE IVC Met 1 | + | 0.09 |
| PDE IVC Met 180 | + | 0.0045 |
| PDE IVA Met 1 | + | 0.155 |
| PDE IVA Met 330 | + | 0.248 |
| Mock transfection | − | 0.006 |

Inhibition of PDE IV in CHO Cells in situ Following Elevation of cAMP.

Figure 5:
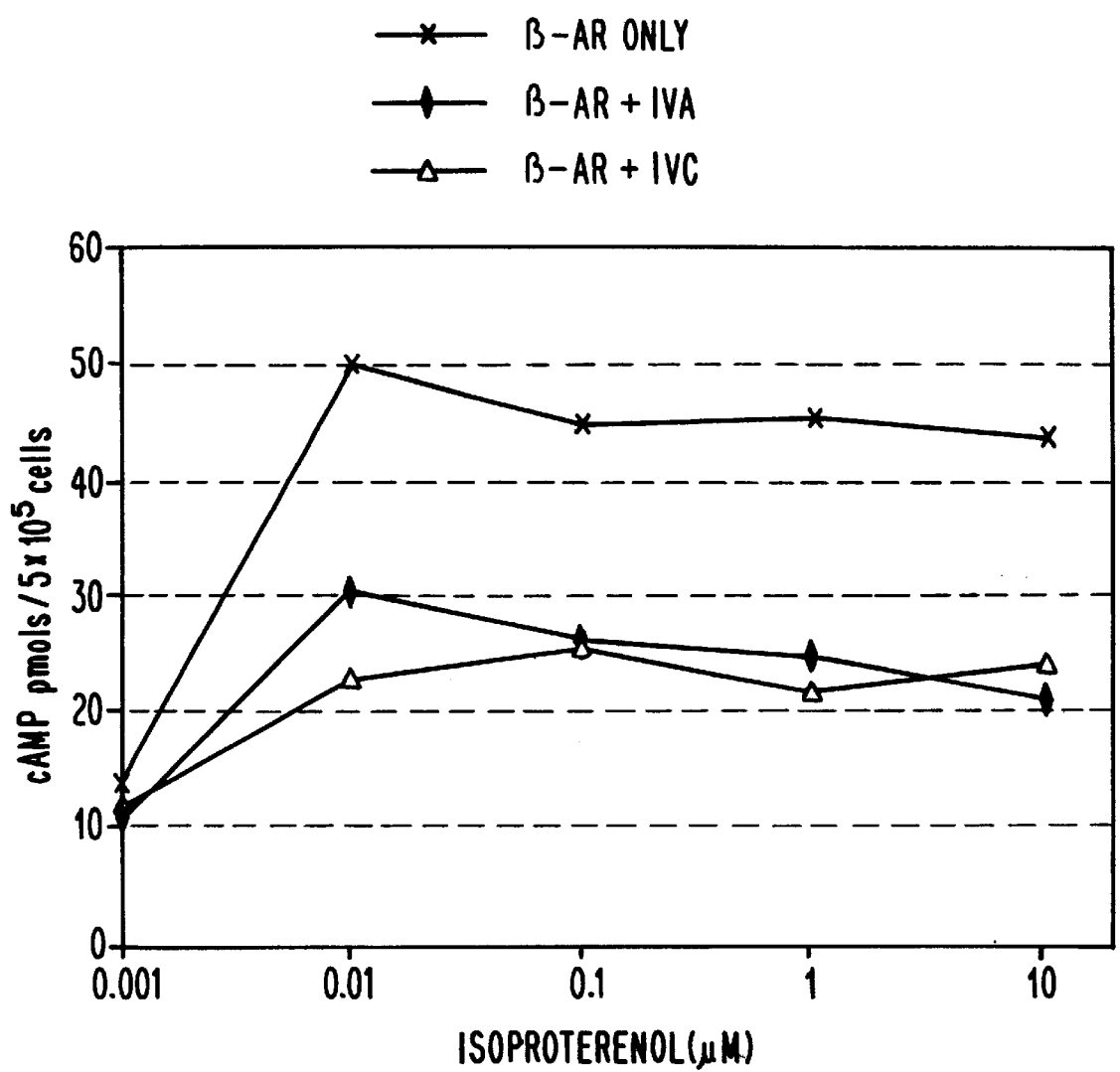
FIG. 5: Elevation of cAMP in CHO cells transfected with beta 2 adrenergic receptor in response to isopreterenol.

A recombinant cell-based assay was developed in order to evaluate the effect of PDE IV inhibitors on the activity of specific PDE IV gene products in situ. Transient expression in CHO cells of a cloned human beta2 adrenergic receptor resulted in a dose-dependent increase in cAMP levels in response to the beta2 agonist, isopreterenol. Cotransfection of either PDE IVC or PDE IVA into the cells prevented this accumulation of cAMP upon stimulation of adenyl cyclase, though the base line level of cAMP was not affected (FIG. 5).

Figure 6:
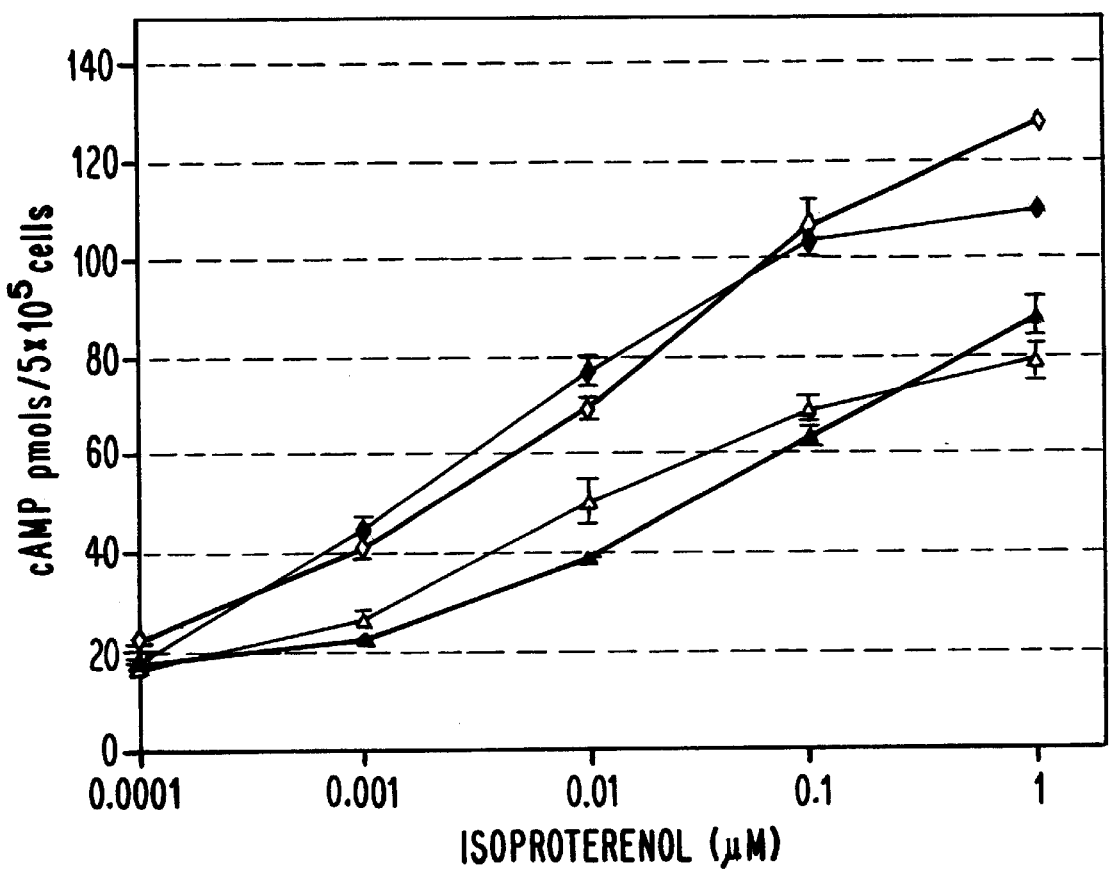
FIG. 6: Effect of R- and S-rolipram on the elevation of CAMP in CHO cells transfected with beta 2 adrenergic receptor +PDE IV C or PDE IVA.
Figure 8:
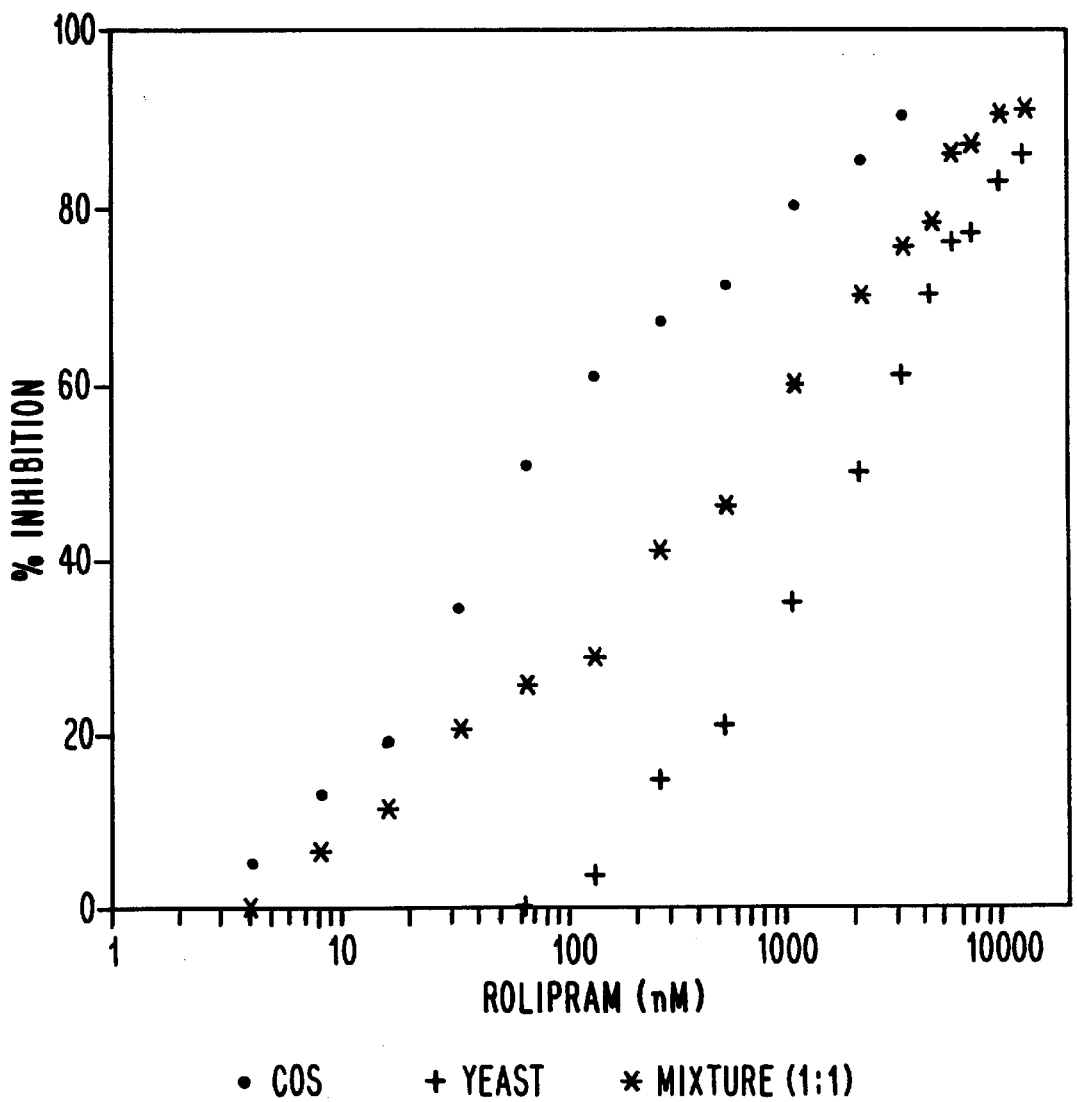
FIG. 8: Inhibition by rolipram of PDE IVC produced in yeast and COS cells and a yeast/COS cell mixture.

This effect was reversed by the addition of rolipram and showed marked enantiomeric selectivity (FIG. 6) This approximately tenfold stereo-selectivity was shown by both A and C and contrasted with the results of in vitro assays on enzymes produced in the same cell type, CHO, in which only PEIVC showed this tenfold selectivity (Table 4).

The significance of this observation is that for a number of biological effects of rolipram both in vitro and in vivo the inhibitor shows marked stereo-selectivity in its potency. For example, R-rolipram is approximately 50 times more effective in the suppression of TNF release-from T lymphocytes (Sommer N. et al. 1995 Nature Medicine L 244–248). Similarly R-rolipram is 15–30 times more potent than S-rolipram in producing behavioural responses in rodent models of depression (e.g. Schmiechen R. et al. 1990 Psychopharmacology 102 17–20). This latter effect is closely correlated with the higher affinity of R-rolipram over S-rolipram for binding sites in the rodent forebrain tissue (Schmiechen et al. ibid.; Kaulen P. et al. 1989 Brain Res. 5003 229–245.). It has been shown that recombinant PDE IV (Torphy T. et al., 1992 J.Biol.Chem. 267 1798–1804) also show stereoselectivity for high affinity binding to rolipram. This indicates that the binding site(s) for rolipram in vivo correspond to a PDE IV(s).

Recombinant human PDE IV enzymes expressed in a mammalian cell system may be assumed to more closely model the native enzyme than the same enzyme produced in a non-mammalian cell host e.g. yeast and bacteria. It appears that both PDE IV A and PDE IVC and probably B and D, show a similar stereoselectivity for inhibition by the PDE IV specific inhibitor rolipram and presumably other close analogues when evaluated in situ. This correlates with some of the biological effects of rolipram in vivo which may be desirable for the development of novel therapies e.g. antiinflammatory and anti-depressive. However, most interestingly and unexpected is the observation herein that only the PDE IVC gene product maintains this rolipram stereoselectivity following extraction from transfected cells. Thus this enzyme advantageously allows the evaluation of the properties of PDE IV inhibitors in an in vitro assay.

What is claimed is:

1. An isolated nucleic acid molecule having the nucleotide sequence depicted in FIG. 1 (SEQ ID No: 31) which encodes a human phosphodiesterase type IVC.

* * * * *

UNITED STATES PATENT AND TRADEMARK OFFICE
CERTIFICATE OF CORRECTION

PATENT NO.    : 6,291,199 B1
DATED         : September 18, 2001
INVENTOR(S)   : Owens et al.

It is certified that error appears in the above-identified patent and that said Letters Patent is hereby corrected as shown below:

Column 1,
Line 39, please delete ""POE" and insert therefor -- PDE --;

Column 2,
Line 15, please delete "etal" and insert therefor -- et al. --;

Column 5,
Line 52, please delete "pic" and insert therefor -- plc --;
Line 67, please delete "5-rolipram" and insert therefor -- S-rolipram --;

Column 6,
Line 43, please delete "R39" and insert therefor -- R3090 --;
Line 56, under Seq. No. 5: please delete
"5 'TTTTTGAATTCGATATCTTCCAGMCCTCAGCGC 3'" and insert therefor
--5 'TTTTTGAATTCGATATCTTCCAGAACCTCAGCGC 3' -- ;
Line 58, under Seq. No. 6: please delete
"5' TTTTTGAATTCCTMGTCCTCTGGTTGTCGAG 3'" and insert therefor
-- 5' TTTTTGAATTCCTAAGTCCTCTGGTTGTCGAG 3' --;
Line 61, under Seq. No. 7: please delete
"5' TTTTTGAATTCAGAGTTGTCTGGTMCCGGC 3'" and insert therefor
-- 5' TTTTTGAATTCAGAGTTGTCTGGTAACCGGC 3' --;
Line 63, under Seq. No. 8: please delete
"5' TTTTGAATTCGTTACGTGTCAGGAGACG 3'" and insert therefor
-- 5' TTTTGAATTCGTTACGTGTCAGGAGAACG 3' --,
Line 66, please delete "CDNA" and insert therefor -- cDNA --;

Column 7,
Line 42, under Seq. No. 10: please delete
"5' TTTCTCGAGGGTrICGGACAGGTGGGTCMCTCCCG-3'" and insert therefor
-- 5'TTTCTCGAGGGTTTCGGACAGGTGGGTCAACTCCCG-3' --;
Line 45, under Seq. No. 11: please delete
"5'-TI CTGAGGCCACTGATCCGGGACATGGGCTG-3'" and insert therefor
-- 5' TTTCTCGAGGCCACTGATCCGGGACATGGGCTG-3' --;

UNITED STATES PATENT AND TRADEMARK OFFICE
CERTIFICATE OF CORRECTION

PATENT NO.   : 6,291,199 B1
DATED        : September 18, 2001
INVENTOR(S)  : Owens et al.

It is certified that error appears in the above-identified patent and that said Letters Patent is hereby corrected as shown below:

Column 8,
Line 41, please delete "(InVftrogen)" and insert therefor -- (InVitrogen) --;

Column 9,
Lines 5 & 6, under Seq. No. 16: please delete
"5' TTTTTGGATCGGCTGGAAGACTGAGCCTGGACC 3'" and insert therefor
-- 5' TTTTTGGATCCGGCTGGAAGACTGAGCCTGGACC 3' --;
Line 9, under Seq. No. 17: please delete
"5' TTTTTCGCATGCCAGCTATGTGGTAGGG 3'" and insert theref
-- 5' TTTTTGGATCCGCATGCCAGCTATGTGGTAGGG 3' --;
Lines 11 &12, under Seq. Id. No. 18: please delete
"5' TTTTTGAATTGGCAGACAAGGGACAGTGAGAAG 3'" and insert therefor
-- 5' TTTTTGAATTCGGCAGACAAAGGGACAGTGAGAAG 3' --;
Lines 21 & 22, under Seq. Id. No. 21: please delete
"5' TTTTTMGCTTCCAAAGTGCATGTCACATGCCAC 3'" and insert therefor
-- 5' TTTTTAAGCTTCCAAAGTGCATGTCACATGCCAC 3' --;
Line 24, under Seq. Id. No. 22: please delete
"5' TTTTTGMTTCGAGGTCAGTGCAGCTCACTGAAC 3'" and insert therefor
-- 5' TTTTTGAATTCGAGGTCAGTGCAGCTCACTGAAC 3' --;
Line 54, under Seq. Id. No. 25: please delete
"5' TTTTTGGATCCATGTCCCAAATCAC 3'" and insert therefor
-- 5' TTTTTGGATCCAGCCCATGTCCCAAATCAC 3' --;

Column 10,
Line 16, please delete "5x10" and insert therefor -- $5 \times 10^5$ --;

UNITED STATES PATENT AND TRADEMARK OFFICE
CERTIFICATE OF CORRECTION

PATENT NO. : 6,291,199 B1
DATED : September 18, 2001
INVENTOR(S) : Owens et al.

It is certified that error appears in the above-identified patent and that said Letters Patent is hereby corrected as shown below:

Column 11,
Line 12, please delete "5CAMP" and insert therefor -- 5' AMP --.
Line 23, under Seq. Id. No. 30: please delete "5'GCGCGCGAATTCTTCTGTITAGTGTTCTGTTGGG 3'" and insert therefor -- 5'GCGCGCGAATTCTCTGTTTAGTGTTCTGTTGGG 3' --;
Line 27, please delete "pRO1 44" and insert therefor -- pRO144 --.

Signed and Sealed this

Seventh Day of January, 2003

JAMES E. ROGAN
*Director of the United States Patent and Trademark Office*